United States Patent
Ackermann et al.

(10) Patent No.: US 10,519,365 B2
(45) Date of Patent: Dec. 31, 2019

(54) LUMINESCENT HYBRID NANOMATERIALS WITH AGGREGATION INDUCED EMISSION

(71) Applicants: Centre National de la Recherche Scientifique, Paris (FR); Université Aix-Marseille, Marseilles (FR); Université de Rennes, Rennes (FR)

(72) Inventors: Jörg Ackermann, Marseilles (FR); Olivier Margeat, Marseilles (FR); Muriel Hissler, Thorigne Fouillard (FR); Pierre Antoine Bouit, Rennes (FR)

(73) Assignees: Centre National de la Recherche Scientifique, Paris (FR); Université Aix-Marseille, Merseille (FR); Université de Rennes 1, Rennes (FR)

( * ) Notice: Subject to any disclaimer, the term of this patent is extended or adjusted under 35 U.S.C. 154(b) by 286 days.

(21) Appl. No.: 15/120,977

(22) PCT Filed: Feb. 24, 2015

(86) PCT No.: PCT/EP2015/053859
§ 371 (c)(1),
(2) Date: Aug. 23, 2016

(87) PCT Pub. No.: WO2015/124802
PCT Pub. Date: Aug. 27, 2015

(65) Prior Publication Data
US 2016/0362601 A1    Dec. 15, 2016

(30) Foreign Application Priority Data

Feb. 24, 2014 (FR) .................................. 14 51470
Jun. 18, 2014 (EP) .................................. 14173001

(51) Int. Cl.
 C09K 11/02    (2006.01)
 C09K 11/54    (2006.01)
 (Continued)

(52) U.S. Cl.
 CPC .......... C09K 11/02 (2013.01); C07F 9/65685 (2013.01); C09K 11/06 (2013.01);
 (Continued)

(58) Field of Classification Search
 CPC ......... C09K 11/02; C09K 11/06; C09K 11/54; B82Y 20/00; C07F 9/6568; C07F 9/65683; C07F 9/65685; C07F 9/65686
 See application file for complete search history.

(56) References Cited

U.S. PATENT DOCUMENTS 7,869,030 B2 *  1/2011  Zhong ............... B82Y 15/00
                                                356/301
8,480,927 B2 *  7/2013  Halpert .............. C09K 11/025
                                                252/301.16
(Continued)

FOREIGN PATENT DOCUMENTS

CN      102874785 A     1/2013
WO     2013/076311 A1   5/2013
(Continued)

OTHER PUBLICATIONS

International Search Report issued in PCT/EP2015/053859 dated May 26, 2015 (2 pages).
(Continued)

Primary Examiner — C Melissa Koslow
(74) Attorney, Agent, or Firm — Osha Liang LLP

(57) ABSTRACT

A luminescent hybrid nanomaterial comprising: at least one inorganic nanomaterial comprising an inorganic first compound; and at least one second compound comprising a first aggregation-induced emission moiety, wherein the at least
(Continued)

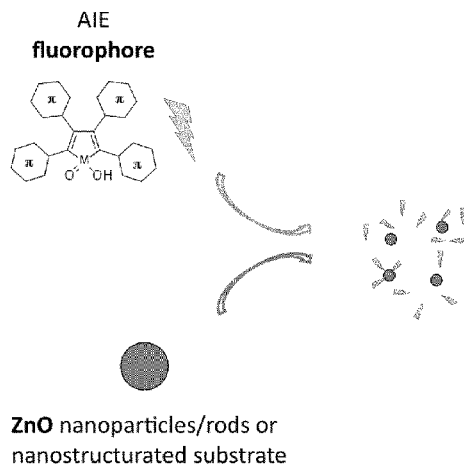

AIE fluorophore

ZnO nanoparticles/rods or nanostructurated substrate

Highly-emissive hybrid material one second compound is grafted on at least part of a surface of the inorganic first compound.

11 Claims, 24 Drawing Sheets

(51) Int. Cl.

| | |
|---|---|
| H05B 33/14 | (2006.01) |
| H01L 51/50 | (2006.01) |
| H01L 51/00 | (2006.01) |
| C07F 9/6568 | (2006.01) |
| C09K 11/06 | (2006.01) |
| H01L 51/44 | (2006.01) |
| B82Y 20/00 | (2011.01) |
| B82Y 40/00 | (2011.01) |

(52) U.S. Cl.
CPC .......... *C09K 11/54* (2013.01); *H01L 51/0071* (2013.01); *H01L 51/502* (2013.01); *B82Y 20/00* (2013.01); *B82Y 40/00* (2013.01); *C09K 2211/1007* (2013.01); *C09K 2211/1096* (2013.01); *H01L 51/5004* (2013.01); *H01L 2251/305* (2013.01); *H01L 2251/552* (2013.01); *Y10S 977/774* (2013.01); *Y10S 977/89* (2013.01); *Y10S 977/95* (2013.01)

(56) References Cited

U.S. PATENT DOCUMENTS

| | | |
|---|---|---|
| 8,491,815 B1 | 7/2013 | DiMaio |
| 2008/0206565 A1 | 8/2008 | Takahashi et al. |
| 2013/0210047 A1 | 8/2013 | Tang et al. |
| 2014/0255696 A1* | 9/2014 | Tang .................. G01N 21/6428 428/402 |

FOREIGN PATENT DOCUMENTS

| | | |
|---|---|---|
| WO | 2013176625 A1 | 11/2013 |
| WO | 2014035159 A1 | 3/2014 |

OTHER PUBLICATIONS

Written Opinion of the International Searching Authority issued in PCT/EP2015/053859 dated May 26, 2015 (5 pages).

Dongdong Li, et al.; "AIE luminogen bridged hollow hydroxyapatite nanocapsules for drug delivery"; Dalton Transactions, RSC Publishing, The Royal Society of Chemistry 2013 pp. 9877-9883 (6 pages).

Office Action issued in the counterpart Chinese Application No. 201580010048.3, dated Nov. 23, 2018 (11 pages).

Office Action issued in the counterpart Chinese Application No. 201580010048.3, dated Jun. 19, 2019 (10 pages).

Office Action issued in the counterpart Japanese Application No. 2016-553880, dated Jan. 8, 2019 (8 pages).

Mahtab Faisal, et al.; "Fabrication of Fluorescent Silica Nanoparticles Hybridized with AIE Luminogens and Exporation of Their Applications as Nanobiosensors in Intracellular Imaging"; Chemistry: A European Journal 2010, pp. 1266-4272 (12 pages).

Mahtab Faisal, et al.; "Fabrication of Silica Nanoparticles with Both Efficient Fluorescence and Strong Magnetization, and Exploration of Their Biological Applications"; Advanced Functional Materials Journal 2011, pp. 1733-1740 (16 pages).

Office Action issued in the counterpart Chinese Application No. 2015800100483., dated Mar. 5, 2018 (10 pages).

* cited by examiner

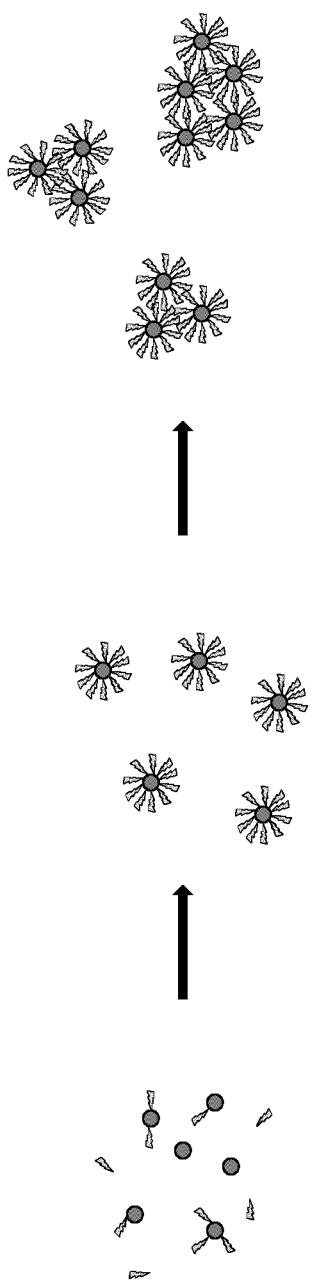
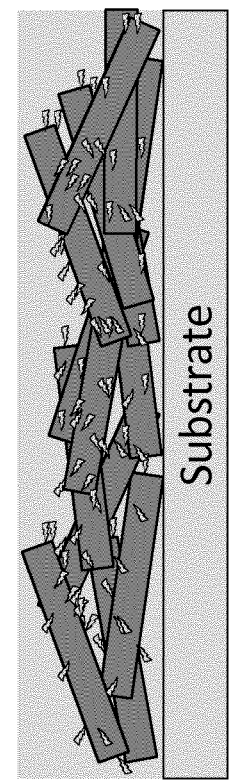
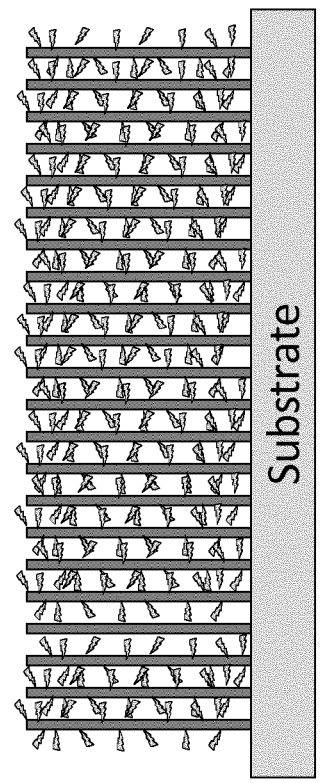
Figure 7a
Figure 7b
Figure 7c

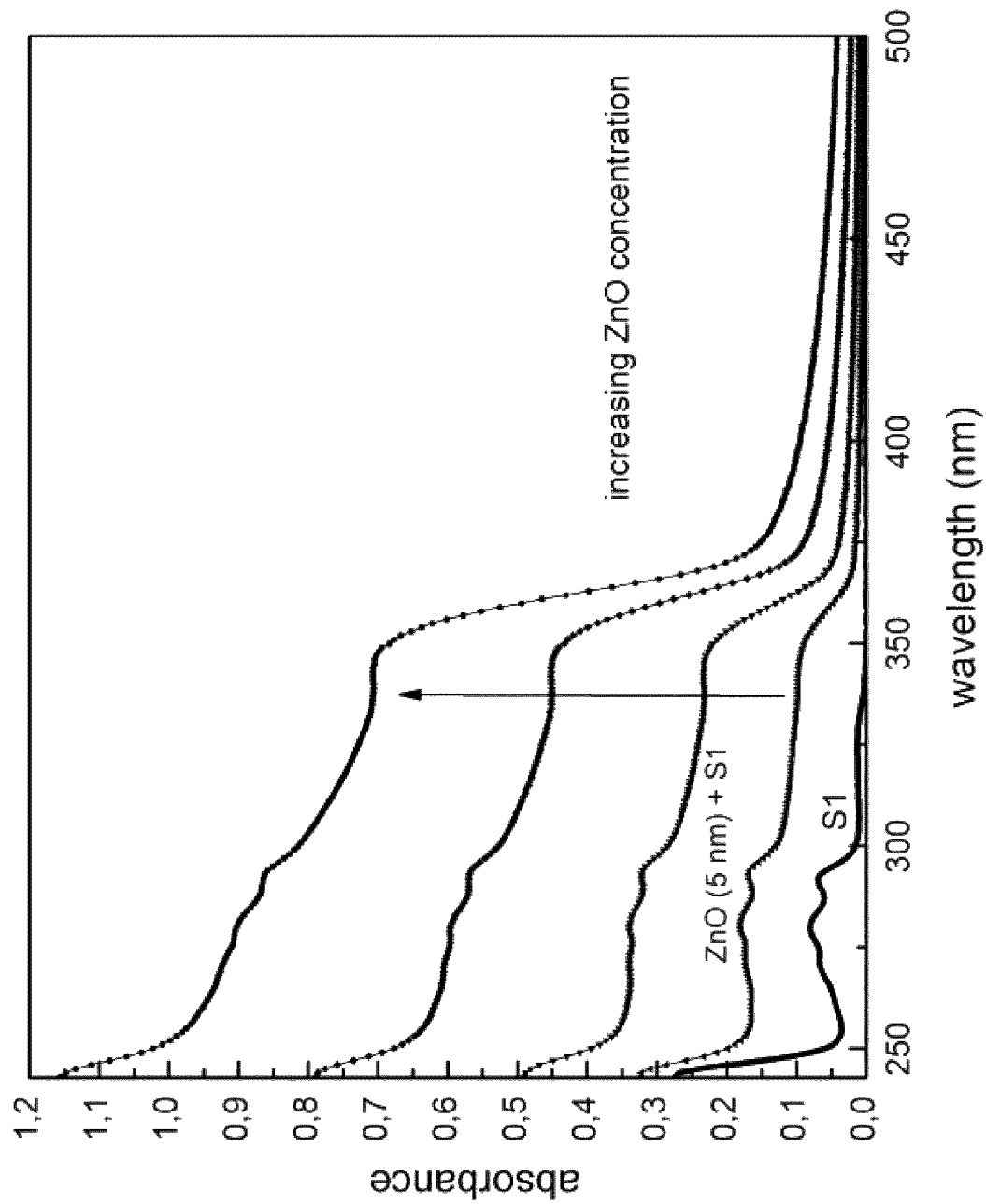

LUMINESCENT HYBRID NANOMATERIALS WITH AGGREGATION INDUCED EMISSION

TECHNICAL FIELD

The present disclosure relates to luminescent hybrid nanomaterials, their process of manufacture, their uses and their applications, particularly but not exclusively for thin films, luminescent solar concentrator, light-emitting hybrid diodes and light-emitting hybrid field-effect transistors.

BACKGROUND

The development of techniques for effective and size selective chemical synthesis of colloidal dispersions of nanocrystals has led to significant advances in the 1990s. These nano-objects (fluorescent semiconductor nanocrystals, metallic nanocrystals, nanotubes, etc.) are nanosized crystals of pure semiconductor material (Si) or composed of type II-VI (CdSe), III-V (GaAs) or others, which, under ultraviolet light, re-emit a fluorescent light. The "color" (wavelength) depends on the size of the nanocrystal. Such emission is a result of the phenomenon called "quantum confinement", which may be observed when the size of the nano-object is very small. More specifically, a nanoparticle may act as structure having discrete physicochemical properties when its size is less than or equal to the Bohr radius of the exciton. Above this radius, the nanoparticles act as inorganic materials having a band structure as shown in FIG. 1. In short, optical properties of nanoparticles (absorption and emission wavelengths) are generally linked to their composition (CdSe, ZnO, etc.) and controlled by their size and shape (sphere, rod, etc.) as shown in FIG. 1. Due to properties of nanoparticles (high absorption in the visible, photoluminescence, etc.), applications are very numerous (biological labeling, materials for light-emitting diodes and solar cells, etc.), and are similar to those of π-conjugated systems.

For example, optical properties of CdSe or CdS nanoparticles or their corresponding core-shell systems CdSe/CdS have attracted much attention during the last decade by the fact that their absorption and emission can be modulated over a large part of the visible spectrum by varying the size and structure of the nanoparticles. As shapes and sizes of CdSe, CdS and CdSe/CdS nanoparticles may be varied over a large range covering dots, rods, tetrapods and multipods of different sizes, their optical properties (absorption and emission wavelength) may also be modified. Generally, applications of CdSe or CdS based nanoparticles concern the field of photovoltaics, light-emitting diodes (LEDs), biology and nano-medicine. However, the toxicity of CdSe or CdS based nanoparticles makes their large-scale applications, such as in bio-medical fields, very difficult.

In contrast to CdSe or CdS based nanoparticles, other inorganic nanoparticles, such as metal oxides (e.g. ZnO nanoparticles, etc.) are known for their non-toxicity, low cost synthesis at large scale and the possibility to synthesize dots, rods, tetrapods and multipods of different sizes, similar to III-V nanoparticles. However, most inorganic nanoparticles, such as ZnO, have a very limited ability to vary their absorption and emission spectra in the visible region due to their wide bandgap. For example, although it is possible to obtain ZnO nanocrystals with emission in the visible region via creation of oxygen defects, this emission, however, needs excitation in the UV range and merely generates a weak fluorescence signal. Furthermore, emission spectrum of most inorganic nanoparticles cannot be modulated over a large range. For example, the emission of ZnO nanocrystals depends greatly on the environment, is not stable and can be extinguished completely.

Compared to nanoparticles, π-conjugated (e.g. semiconducting) organic systems are functional materials of interest for applications in less expensive and flexible electronic devices such as light-emitting diodes (OLEDs), field effect transistors (OFETs) and photovoltaic solar cells. This interest is mainly due to the possibility of modifying physical properties and supramolecular organization of π-conjugated organic systems via molecular structural variations. Predictive structure-property relationships may be established to suit a desired function via chemical engineering at the molecular level. For example, the development of advanced electroluminescent organic materials is possible following seminal reports of efficient organic light-emitting diodes (OLEDs) based on small molecules and conjugated polymers. However, varying the chemical composition of conjugated systems is a major concern to control their properties. Indeed, the optical and electronic properties of bulk material generally depend on the chemical structure of the conjugated monomeric/oligomeric/polymeric carbon backbone (HOMO-LUMO gap, electronic density, etc.) and on the interaction between the individual molecules (supramolecular arrangement, morphology). For example, luminescence processes for organic luminophores are generally concentration dependent. For most of the cases, the luminescence is weakened or totally quenched in concentrated solutions.

Since the last decade, a new field of so called hybrid nanomaterials has emerged that aims to combine the advantages of organic materials with inorganic nanocrystals allowing to generate new functionality via synergetic effects. Hybrid nanomaterials using ZnO nanoparticles as template were used in the past to assemble 1D and 2D nanoparticles with optical, electronic and photovoltaic properties. In this case, π-conjugated ligands were grafted onto the surface of ZnO nanoparticles of either spherical and rod-like shape leading to hybrid nanomaterials with opto-electronic properties governed by both the organic and inorganic component of the nanomaterial. For example, light absorption of ZnO nanoparticles could be increased in the visible via grafting organic dyes onto their surface. However fluorescence or phosphorescence emission of the dye that would allow the modulation of the emission properties of ZnO, are usually either quenched by exciton dissociation at the ZnO/dye interface due to the formation of a hybrid heterojunction or quenched due to the formation of dye aggregates at the surface of the inorganic component.

Accordingly, there exists a continuing need to provide luminescent hybrid nanomaterials; easy processes to manufacture the same; and thin films, luminescent solar concentrators, light-emitting hybrid diodes and light-emitting hybrid field-effect transistors comprising the same.

SUMMARY

An object of the present disclosure is to provide a luminescent hybrid nanomaterial which may be comprised, particularly but not exclusively, in a thin film, a luminescent solar concentrator, a light-emitting hybrid diode or a light-emitting hybrid field-effect transistor. Still another object of the present disclosure is to provide a process of manufacture of a luminescent hybrid nanomaterial which can be performed with high yield, under mild conditions and in a limited number of steps.

According to a first aspect, the above-mentioned objects, as well as further advantages, are achieved by a luminescent hybrid nanomaterial comprising: at least one inorganic nanomaterial comprising an inorganic first compound; and at least one second compound comprising a first aggregation-induced emission moiety, wherein the at least one second compound is grafted on at least part of a surface of the inorganic first compound.

According to a second aspect, the above-mentioned objects, as well as further advantages, are achieved by a luminescent hybrid nanomaterial comprising: at least one inorganic nanomaterial comprising an inorganic first compound; and at least one second compound having one of the following structures:

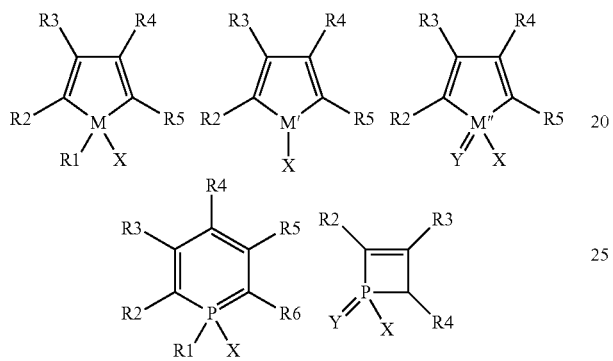

wherein:

M is selected from the group comprising Si, Ge, Sn and Pb;

M' is selected from the group comprising P, As, Sb and Bi;

M" is selected from the group comprising Si, Ge, Sn, Pb, P, As, Sb and Bi;

X is selected from the group comprising H, OH SH, SeH and TeH, or X is selected from the group comprising OR', SR', SeR' and TeR', R' being a first linker, the first linker comprising a first anchoring group, the first linker being a linear, cyclic or branched, saturated or unsaturated, C1-C20 alkyl group, the first anchoring group being selected from the group comprising a hydroxyl, thiol, carboxylic acid, carboxylic acid ester, cyano, amino, amido, sulfinic acid, sulfonic acid, phosphonic acid, dithiophosphinic acid, phosphate, phosphoester, phosphothioester, phosphine oxide, phosphine sulfide, phosphine, and silanol group;

Y is selected from the group comprising O, S, Se and Te;

R1 is selected from the group comprising a cyano, amino, amido, carboxylic acid, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, C2-C20 carboxylic acid ester, C1-C20 alkylsulfinic acid, C1-C20 alkylsulfonic acid, C1-C20 alkylphosphonic acid, C1-C20 alkyldithiophosphinic acid, C1-C20 alkylphosphate, C1-C20 alkylphosphoester, C1-C20 alkylphosphine oxide, and C1-C20 alkylphosphine group; or R1 is selected from the group comprising H, OH SH, SeH and TeH, or R1 is selected from the group comprising OR", SR", SeR" and TeR", R" being a second linker comprising a second anchoring group, the second linker being a linear, cyclic or branched, saturated or unsaturated, C1-C20 alkyl group, the second anchoring group being selected from the group comprising a hydroxyl, thiol, carboxylic acid, carboxylic acid ester, cyano, amino, amido, sulfinic acid, sulfonic acid, phosphonic acid, dithiophosphinic acid, phosphate, phosphoester, phosphothioester, phosphine oxide, phosphine sulfide, phosphine, and silanol group; and each R2 to R6 is independently selected from the group comprising a hydrogen, hydroxy, nitro, nitroxy, nitroso, halide, cyano, isothiocyanato, amino, amido, imino, azido, cyanato, isocyanato, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, carboxylic acid, C2-C20 carboxylic acid ester, sulfinic acid, C1-C20 alkylsulfinyl, sulfonic acid and C1-C20 alkylsulfonyl group, wherein the at least one second compound is grafted on at least part of a surface of the inorganic first compound.

According to a third aspect, one or more of the above-mentioned objects may be achieved by a process of manufacture of a luminescent hybrid nanomaterial according to the first aspect or the second aspect, the process comprising: providing the at least one inorganic nanomaterial comprising the inorganic first compound; providing the at least one second compound; contacting the at least one second compound to at least part of the surface of the inorganic first compound under conditions appropriate to graft or physisorb the at least one second compound on the surface of the inorganic first compound.

According to a fourth aspect, one or more of the above-mentioned objects may be achieved by a thin film, a luminescent solar concentrator, a light-emitting hybrid diode or a light-emitting hybrid field-effect transistor comprising a luminescent hybrid nanomaterial according to the first aspect or the second aspect or a luminescent hybrid nanomaterial manufactured by the process according to the third aspect.

According to a fifth aspect, one or more of the above-mentioned objects may be achieved by a use of a luminescent hybrid nanomaterial according to the first aspect or the second aspect or a luminescent hybrid nanomaterial manufactured by the process according to the third aspect to manufacture a product according to the fourth aspect.

Other aspects and advantages of the present disclosure will be apparent from the following Figures, description and appended claims.

BRIEF DESCRIPTION OF DRAWINGS

The present invention will be better understood and other advantages and particularities will become clear on reading the description that follows, given purely by way of indication and in no way limiting, and by referring to the appended figures in which:

FIG. 7a shows a grafting process according to the present disclosure in the case of luminescent hybrid nanomaterials obtained in solution. FIGS. 7b-c show luminescent hybrid nanomaterials obtained via a grafting process according to the present disclosure of the second compound onto the surface of a nanostructured inorganic substrate (b) or inorganic nanoporous substrate (c).

FIGS. 10a-b show absorption (a) and fluorescent (b) spectra of inorganic nanoparticles grafted with a comparative organic compound S1 with increasing concentration of ZnO.

DETAILED DESCRIPTION OF EMBODIMENTS

Figure 1:
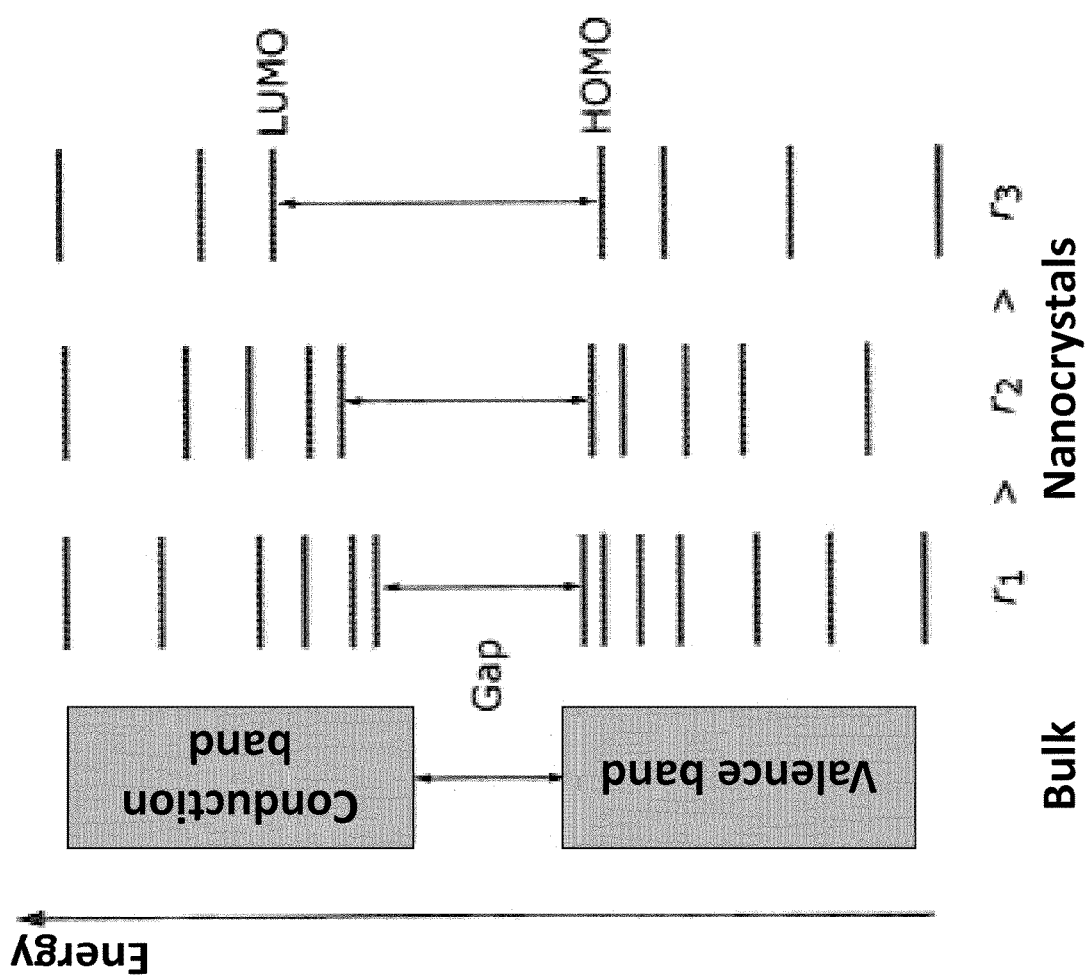
FIG. 1 shows schematic views of light emission of a classical nanoparticle as a function of size.

Embodiments of the present disclosure will now be described in detail with reference to the accompanying Figures. In the following detailed description of embodiments of the present disclosure, numerous specific details are set forth in order to provide a more thorough understanding of the present disclosure. However, it will be apparent to one of ordinary skilled in the art that the present disclosure may be practiced without these specific details. In other instances, well-known features have not been described in detail to avoid unnecessarily complicating the description.

Herein, the words "comprise/comprising" are synonymous with (means the same thing as) "include/including," "contain/containing", are inclusive or open-ended and do not exclude additional, non-recited elements. Further, herein the term "about" and "substantially" are synonymous with (means the same thing as) a 20% margin of the respective value.

In the following, it is meant by "nanomaterial" a nanoparticle, a nanostructure or a material having a large surface area to volume ratio such as greater than about 6 $\mu m^{-1}$. In the following, it is meant by "hybrid" comprising an inorganic component and an organic component. In the following, it is meant by "organic compound" a compound consisting mainly of carbon and hydrogen and containing to a lower extent other elements such as one or more O, N, S, P, Si, B, Se, Ge, Sn, Pb, As, Sb and Bi, except elemental carbon, carbonates, carbon oxide and carbon cyanide molecules. In the following, it is meant by "organometallic compound" an organic compound comprising at least one metal. In the following, it is meant by "inorganic compound" a compound which is neither organic nor organometallic. In the following, it is meant by "grafting" a process of linking molecules onto a solid surface, involving electrostatic interaction and/or covalent binding. In the following, it is meant by "physisorption" a process of linking molecules onto a solid surface, involving van der Waals forces. In the following, it is meant by "luminescent" fluorescent and/or phosphorescent. In the following, it is meant by "nanosystem" and "nanohybrid" a luminescent hybrid nanomaterial according the present disclosure. In the following, it is meant by "aggregation-induced emission (AIE) moiety" a moiety presenting an AIE phenomenon. In the following, it is meant by "moiety presenting an AIE phenomenon" a compound presenting a restriction of intramolecular rotations (RIR), formation of J-aggregates and/or having intramolecular planarization or restriction of the transition from the local excited state to the intramolecular charge transfer state that accompanies twisting after or before grafting or physisorption on the inorganic compound that induces an enhancement of the luminescence. In the following, it is meant by "heteroatom" an atom other than a carbon or a hydrogen such as an atom selected from the group comprising O, N, S, P, Si, B, Se, Ge, Sn, Pb, As, Sb and Bi. In the following, it is meant by "cyclic conjugated substituent" a π or σ-π conjugated system. In the following, it is meant by "oligomer" a compound having 2 to 20 identical (homo-oligomers) or different (co-oligomers) repeating units. In the following, it is meant by "polymer" a compound having more than 20 identical (homo-polymers) or different (co-polymers) repeating units. In the following, it is meant by "connecting" the chemical bonding, for example by way of a covalent bond, of a chemical moiety or of a chemical group to another chemical moiety or chemical group.

As described in the background section, the development of luminescent organic, inorganic and hybrid nanomaterials remains limited. However, the Applicants have found that compounds bearing an aggregation-induced emission moiety (herein referred as the second compound) may be grafted on inorganic nanomaterials to exalt both the optical properties of the second compounds and the properties of the inorganic nanomaterials thereby providing new high-performance materials.

The luminescent hybrid nanomaterial according to the present disclosure may comprise at least one inorganic nanomaterial comprising an inorganic first compound; and at least one second compound comprising a first aggregation-induced emission moiety, wherein the at least one second compound is grafted on at least part of a surface of the inorganic first compound.

Figure 2:
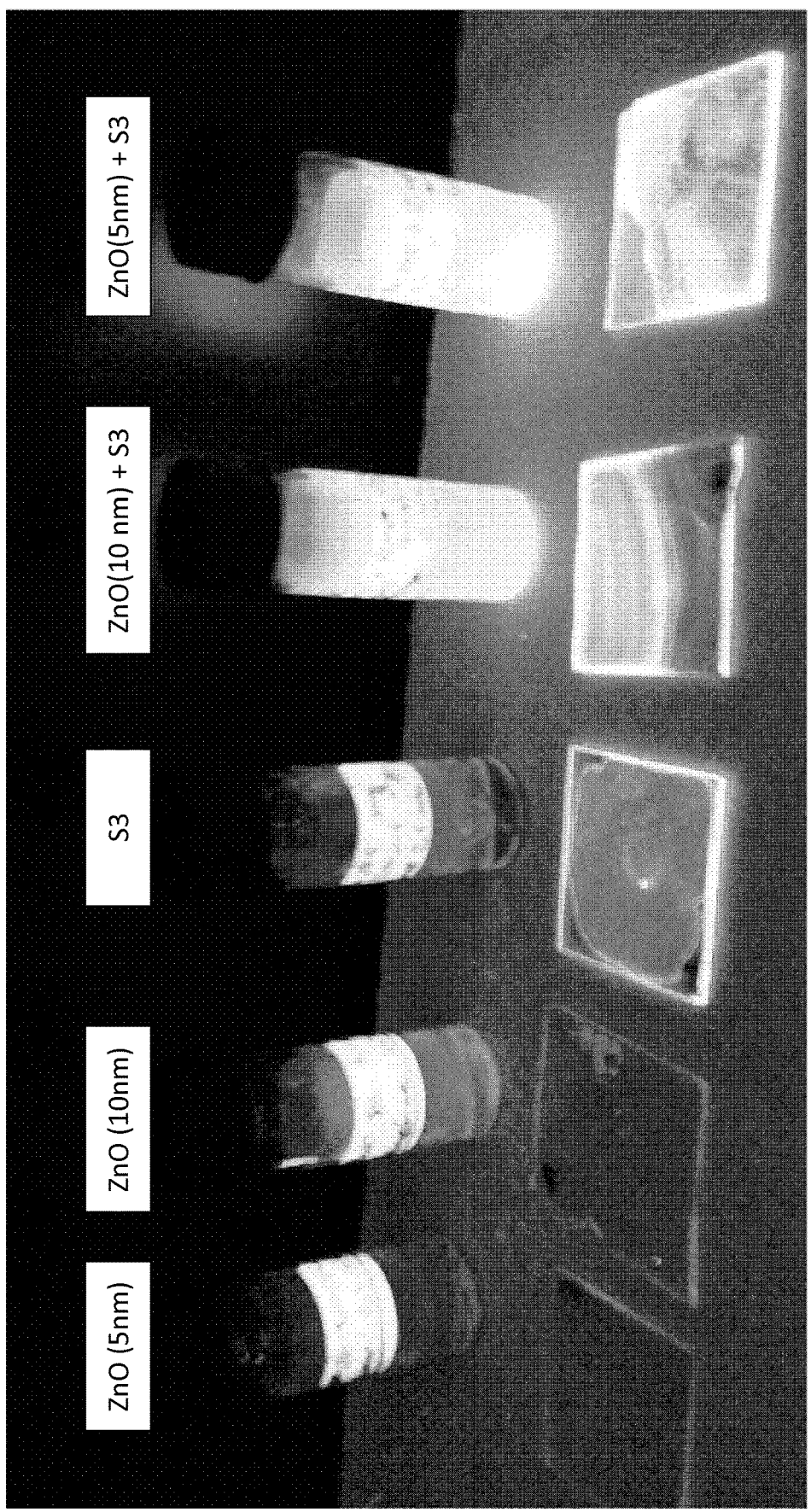
FIG. 2 shows a photography of different glass vessels and thin films comprising inorganic nanomaterials of different size and shape, second compounds and luminescent hybrid nanomaterials according to the present disclosure under illumination at 365 nm.
Figure 3:
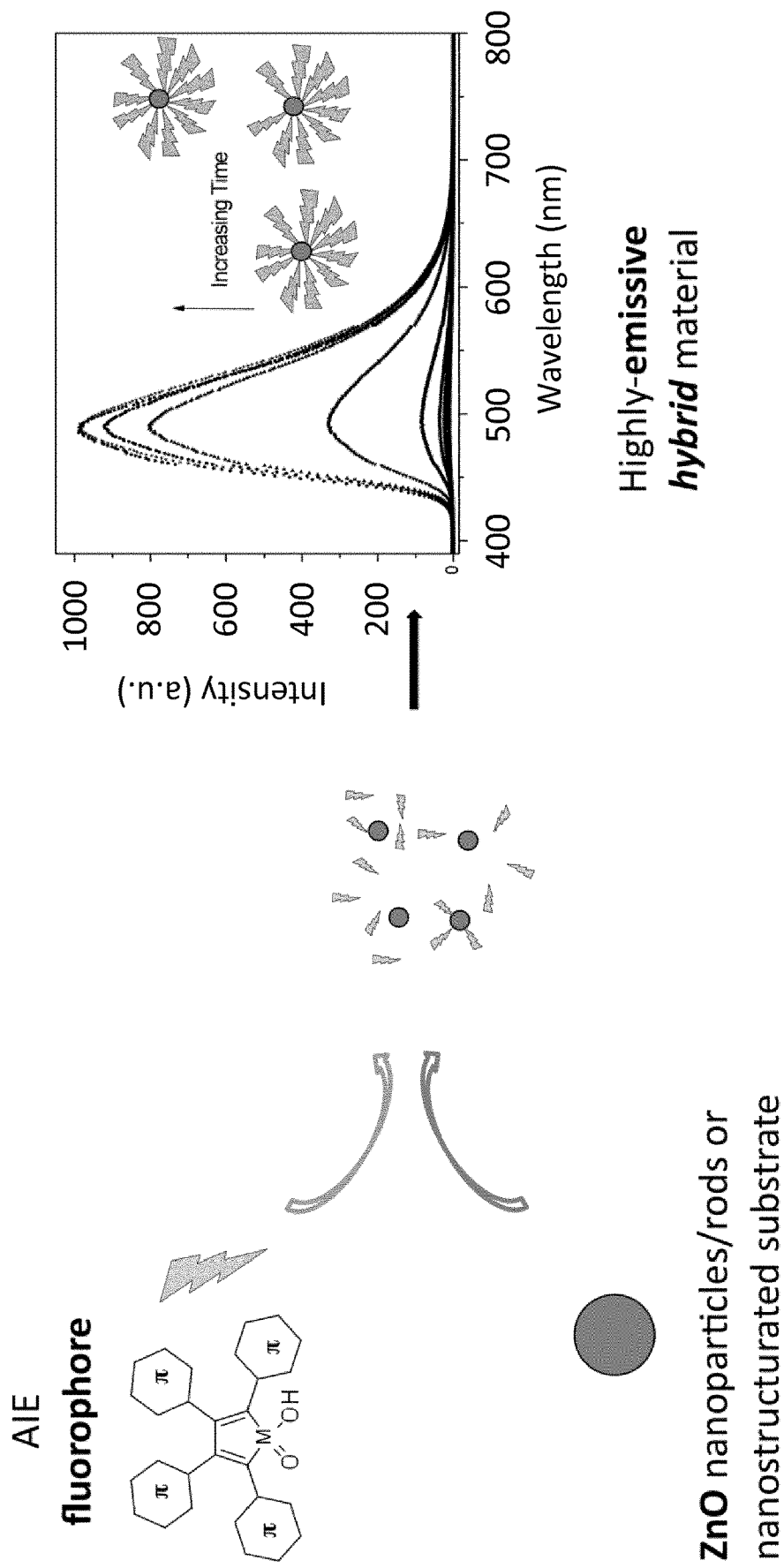
FIG. 3 shows a grafting process and time evolution of emission intensity of a luminescent hybrid nanomaterial according to the present disclosure.

Indeed, the Applicants have found that a luminescent hybrid nanomaterial may be obtained by grafting or physisorb the second compound, such as an organic or organometallic molecule, which may have for example an initially low fluorescence efficiency, onto the inorganic nanomaterial, such as a ZnO nanoparticle, by simply mixing the second compound and the inorganic nanomaterial, for example in solution. After grafting of the second compound, the resulting luminescent hybrid nanomaterial shows very strong emission intensity due to aggregation of the compounds at the surface. FIG. 2 shows an exemplary photograph of various glass vials containing ZnO nanoparticles of different sizes (5 nm and 10 nm), an exemplary organic second compound S3, the structure of which may be found in the EXAMPLE section, and mixtures of S3 with ZnO nanoparticles. In this example, each solution were deposited on glass and placed in front of each vial to compare fluorescence in solution and in thin film. Also, in this example, all samples are excited with a UV light of a wavelength of 380 nm. It can be seen that both the fluorescence of the ZnO nanoparticles alone and of S3 alone are very low, whether in solution, such as in THF, $CHCl_3$, or MeOH, or on a thin layer. However, after grafting S3 at the surface of ZnO nanoparticles, such as simply mixing together S3 and ZnO nanoparticles in solution, the fluorescence is greatly amplified. As shown in the time resolved fluorescence spectrum of FIG. 3, the grafting of a second compound, such as an exemplary heterole, on at least part of a surface an inorganic first compound, such as an exemplary ZnO nanoparticle, provides highly emissive luminescent hybrid nanomaterials. For example, as shown in FIGS. 5a-f, according to one or more embodiments, fluorescence amplification by a factor of for example 300 may be obtained for luminescent hybrid nanomaterials according to the present disclosure, which corresponds to about 20% of absolute quantum yield of the grafted the second compound. In addition, the light emission also remains very intense in a thin layer exposed to air.

Simply put, the luminescent hybrid nanomaterials according to the present disclosure provide new properties to fluorescent materials that allow improving and enlarging the field of applications of fluorescent materials. These luminescent hybrid nanomaterials were developed by synthesizing exemplary second compounds and inorganic nanomaterials, in which the inorganic nanomaterials are used as template for the formation of nanohybrids via grafting or physisorption of the second compound thereby providing luminescent hybrid nanomaterials according to the present disclosure.

In one or more embodiments, the second compound may be organic or organometallic. In one or more embodiments, the first aggregation-induced emission moiety may comprise a first cyclic conjugated substituent; and a second substituent conjugated with the first cyclic conjugated substituent. In one more embodiment, the first cyclic conjugated substituent may be a heterole such as phosphole or an aryl group such as a phenyl group. In one or more embodiments, the second substituent may be cyclic such as an aryl group. In one or more embodiments, the first aggregation-induced emission moiety may further comprise a linking moiety selected from the group comprising an ether, a linear C1-C2 alkyl, C2 alkenyl and C2 alkynyl group, the linking moiety connecting the first cyclic conjugated substituent to the second substituent. In one or more embodiments, the linking moiety may further comprise one or more heteroatoms such as one or more oxygen atoms.

In one or more embodiment, the at least one second compound may comprise at least one anchoring moiety, or at least one linker comprising at least one anchoring group. For example, in one or more embodiment, the at least one second compound may comprise a first and optionally a second or more anchoring moieties, or a first linker comprising at least one first anchoring group and optionally a second or more linkers comprising a second or more anchoring groups. According to these embodiments, the anchoring moiety or anchoring group may be configured to graft the first aggregation-induced emission moiety to the surface of the inorganic nanomaterial by chemical grafting or physisorption. For example, the first linker, the second linker and any additional linker may be a linear, cyclic or branched, saturated or unsaturated, C1-C20 alkyl group. In one or more embodiments, the linkers (e.g. the first linker) may further comprise one or more heteroatoms. According to these embodiments, a controlled and ordered molecular assembly may advantageously be formed, thereby providing, for example by adsorption, a single layer of molecules onto a solid surface. Furthermore, to modify or enhance properties of the luminescent hybrid nanomaterial, it may be possible to incorporate anchoring groups or moieties having a function with a greater or lesser affinity with the surface of the inorganic nanoparticle.

In one or more embodiment, the first and/or second anchoring moiety may be selected from the group comprising M(X)R1, M'X, M"(X)Y, wherein M is selected from the group comprising Si, Ge, Sn and Pb M' is selected from the group comprising P, As, Sb and Bi; M" is selected from the group comprising Si, Ge, Sn, Pb, P, As, Sb and Bi; X is selected from the group comprising H, OH SH, SeH; Y is selected from the group comprising O, S, Se and Te; and R1 is selected from the group comprising a cyano, amino, amido, carboxylic acid, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, C2-C20 carboxylic acid ester, C1-C20 alkylsulfinic acid, C1-C20 alkylsulfonic acid, C1-C20 alkylphosphonic acid, C1-C20 alkyldithiophosphinic acid, C1-C20, alkylphosphate, C1-C20 alkylphosphoester, C1-C20 alkylphosphine oxide, and C1-C20 alkylphosphine group, or R1 is selected from the group comprising H, OH, SH, SeH and TeH, or R1 is selected from the group comprising OR", SR", SeR" and TeR", R" being a second linker comprising a second anchoring group. For example, in one or more embodiments, the first anchoring moiety may be comprised in the first cyclic conjugated substituent. For example, the first anchoring moiety may be Si(O)OH, P(O)OH, P(S)OH, P(S)SH, P(O)R1, P(S)R1, P(O)OR P(S)OR, P(S)SR, wherein R1 is as described herein above and R is selected from the group comprising a C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, C2-C20 carboxylic acid ester, C1-C20 alkylsulfinic acid, C1-C20 alkylsulfonic acid, C1-C20 alkylphosphonic acid, C1-C20 alkyldithiophosphinic acid, C1-C20 alkylphosphate, C1-C20 alkylphoester, C1-C20 alkylphosphine oxide and C1-C20 alkylphosphine group.

In one or more embodiments, the first and/or second anchoring group may be selected from the group comprising a hydroxyl, thiol, carboxylic acid, carboxylic acid ester, cyano, amino, amido, sulfinic acid, sulfonic acid, phosphonic acid, C1-C20 alkyldithiophosphinic acid, phosphate, phosphoester, phosphothioester, phosphine oxide, phosphine sulfide, phosphine, and silanol group.

In one or more embodiments, the at least one second compound may further comprise a third substituent connected to the first aggregation-induced emission moiety. In one or more embodiments, the third substituent may be connected and optionally conjugated with the first aggregation-induced emission moiety and/or to a second aggregation-induced emission moiety and/or to an additional substituent. For example, the third substituent may be an additional cyclic conjugated moiety configured for modifying the emission spectra of the luminescent hybrid nanomaterial. For example, the third substituent may be a C6-C20 aryl, a C4-C20 heteroaryl, a C7-C20 alkylaryl, or a C7-C20 arylalkyl group.

In one or more embodiments, the luminescent hybrid nanomaterial may be configured to generate white light. White is the color the human eye sees when it senses light which contains all the wavelengths of the visible spectrum. It can be produced by mixing the primary colors of light: red, green and blue (RGB) or by mixing two complementary colors (For example: mixing blue and orange emitters), a process called additive mixing. In the case of the invention, in one or more embodiments, the at least one second compound may further comprise a second aggregation-induced emission moiety. For example, the second aggregation-induced emission moiety may be connected to the first aggregation-induced emission moiety, to the third substituent or to an additional substituent. According to these embodiments, complementary emission properties of the two or more aggregation-induced emission moieties may generate white light.

In one or more embodiments, the at least one second compound may further comprise at least one additional substituent selected from the group comprising a solubilizing moiety, a self assembly group, a chiral group, an oligomer and a polymer. For example, the at least one additional substituent may be connected to the first aggregation-induced emission moiety, to the second aggregation-induced emission moiety or to the third substituent.

In one or more embodiments, the at least one second compound may have one of the following structures:

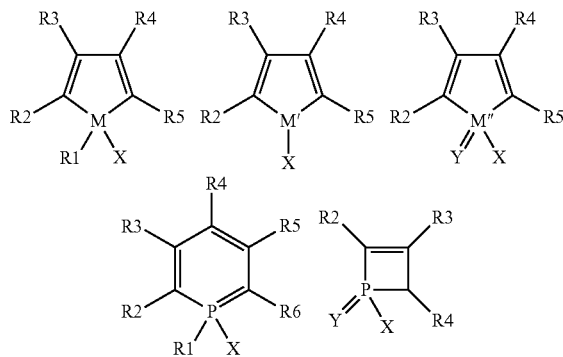

wherein:
M is selected from the group comprising Si, Ge, Sn and Pb;
M' is selected from the group comprising P, As, Sb and Bi;
M" is selected from the group comprising Si, Ge, Sn, Pb, P, As, Sb and Bi;
X is selected from the group comprising H, OH SH, SeH and TeH, or X is selected from the group comprising OR', SR', SeR' and TeR',
R' being a first linker, the first linker comprising a first anchoring group, the first linker being a linear, cyclic or branched, saturated or unsaturated, C1-C20 alkyl group,
the first anchoring group being selected from the group comprising a hydroxyl, thiol, carboxylic acid, carboxylic acid ester, cyano, amino, amido, sulfinic acid, sulfonic acid, phosphonic acid, dithiophosphinic acid, phosphate, phosphoester, phosphothioester, phosphine oxide, phosphine sulfide, phosphine, and silanol group;
Y is selected from the group comprising O, S, Se and Te;
R1 is selected from the group comprising a cyano, amino, amido, carboxylic acid, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, C2-C20 carboxylic acid ester, C1-C20 alkylsulfinic acid, C1-C20 alkylsulfonic acid, C1-C20 alkylphosphonic acid, C1-C20 alkyldithiophosphinic acid, C1-C20 alkylphosphate, C1-C20 alkylphosphoester, C1-C20 alkylphosphine oxide, and C1-C20 alkylphosphine group; or R1 and is selected from the group comprising H, OH SH, SeH and TeH, or R1 is selected from the group comprising OR", SR", SeR" and TeR",
R" being a second linker comprising a second anchoring group,
the second linker being a linear, cyclic or branched, saturated or unsaturated, C1-C20 alkyl group,
the second anchoring group being selected from the group comprising a hydroxyl, thiol, carboxylic acid, carboxylic acid ester, cyano, amino, amido, sulfinic acid, sulfonic acid, phosphonic acid, dithiophosphinic acid, phosphate, phosphoester, phosphothioester, phosphine oxide, phosphine sulfide, phosphine, and silanol group; and
each R2 to R6 is independently selected from the group comprising a hydrogen, hydroxy, nitro, nitroxy, nitroso, halide, cyano, isothiocyanato, amino, amido, imino, azido, cyanato, isocyanato, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, carboxylic acid, C2-C20 carboxylic acid ester, sulfinic acid, C1-C20 alkylsulfinyl, sulfonic acid and C1-C20 alkylsulfonyl group.

In one or more embodiments, the first linker and/or the second linker further comprise one or more heteroatoms. In one or more embodiments, R2 and R3, or R3 and R4, or R4 and R5, or R5 and R6 form together a ring system. Preferably, only one of R2-R3, R3-R4, R4-R5, and R5-R6 form a ring system.

In one or more embodiments, at least one of R2 to R6 may be selected from the group comprising a C6-C20 aryl, C4-C20 heteroaryl, C7-C20 arylalkyl, C8-C20 arylalkenyl, C8-C20 arylalkynyl, C6-C20 haloaryl. For example, at least one of R2 to R6 may be substituted by at least one functional group selected from the group comprising a hydrogen, hydroxy, nitro, nitroxy, nitroso, halide, cyano, isothiocyanato, amino, amido, imino, azido, cyanato, isocyanato, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, carboxylic acid, C2-C20 carboxylic acid ester, sulfinic acid, C1-C20 alkylsulfinyl, sulfonic acid and C1-C20 alkylsulfonyl group.

In one or more embodiments, at least one of R2 to R6 may be selected from the group comprising a fluorene, stilbene, naphtalene, pyridine, oligopyridine, furane, oligofurane, anthracene, phenanthrene, triphenylene, benzofurane, benzothiophene, quinoline, phenyl pyridine, isoquinoline, indole, phenyl, oligophenyl, oligophenylene-vinylene, thiophene, oligothiophene, and oligothiophene-vinylene group.

In one or more embodiments, M may be Si; M' may be P; M" may be Si or P; X may be OH or SH; and Y may be O or S.

In one or more embodiments, the at least one second compound has one of the following structures:

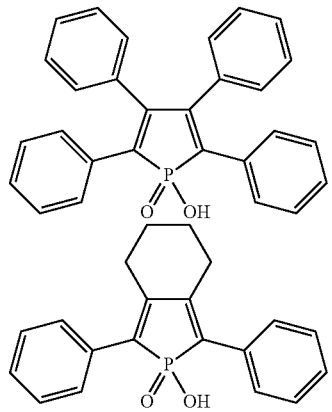

In one or more embodiments, the at least one second compound may have the following structure:

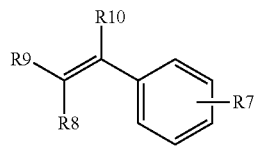

wherein:
R7 is a first linker comprising a first anchoring group, the first linker being a linear, cyclic or branched, saturated or unsaturated, C1-C20 alkyl group,
the first anchoring group being selected from the group comprising a hydroxyl, thiol, carboxylic acid, carboxylic acid ester, cyano, amino, amido, sulfinic acid, sulfonic acid, phosphonic acid, phosphate, phosphoester, dithiophosphinic acid, phosphothioester, phosphine oxide, phosphine sulfide, phosphine, and silanol group; and
each R8 to R10 is independently selected from the group comprising a hydrogen, hydroxy, nitro, nitroxy, nitroso, halide, cyano, isothiocyanato, amino, amido, imino, azido, cyanato, isocyanato, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, carboxylic acid, C2-C20 carboxylic acid ester, sulfinic acid, C1-C20 alkylsulfinyl, sulfonic acid and C1-C20 alkylsulfonyl group.

In one or more embodiments, each R8 to R10 is independently selected from the group comprising a hydroxy, nitro, nitroxy, nitroso, halide, cyano, isothiocyanato, amino, amido, imino, azido, cyanato, isocyanato, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, carboxylic acid, C2-C20 carboxylic acid ester, sulfinic acid, C1-C20 alkylsulfinyl, sulfonic acid and C1-C20 alkylsulfonyl group.

In one or more embodiments, at least one of R8 to R10 may be selected from the group comprising fluorene, stilbene, naphtalene, pyridine, oligopyridine, furane, oligofurane, anthracene, phenanthrene, triphenylene, benzofurane, benzothiophene, quinoline, phenyl pyridine, isoquinoline, indole, phenyl, oligophenyl, oligophenylene-vinylene, thiophene, oligothiophene, and oligothiophene-vinylene group.

In one or more embodiments, the first anchoring group is selected from the group comprising a hydroxyl, thiol, carboxylic acid, carboxylic acid ester, cyano, amido, sulfinic acid, sulfonic acid, phosphonic acid, phosphate, phosphoester, dithiophosphinic acid, phosphothioester, phosphine oxide, phosphine sulfide, phosphine, and silanol group.

In one or more embodiments, the first anchoring group is selected from the group comprising a hydroxyl, thiol, carboxylic acid, carboxylic acid ester, cyano, amido, sulfinic acid, sulfonic acid, phosphonic acid, phosphate, phosphoester, dithiophosphinic acid, phosphothioester, phosphine oxide, phosphine sulfide, phosphine, and silanol group; and
each R8 to R10 is independently selected from the group comprising a hydroxy, nitro, nitroxy, nitroso, halide, cyano, isothiocyanato, amino, amido, imino, azido, cyanato, isocyanato, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, carboxylic acid, C2-C20 carboxylic acid ester, sulfinic acid, C1-C20 alkylsulfinyl, sulfonic acid and C1-C20 alkylsulfonyl group.

In one or more embodiments, R7 may be a carboxylic acid. For example, the at least one second compound has the following structure:

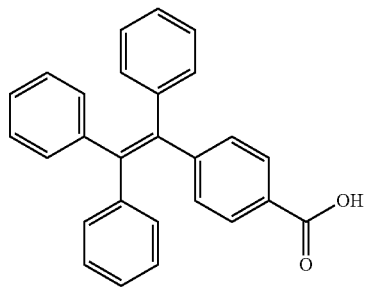 [SMILES: O=C(O)c1ccc(C(=C(c2ccccc2)c2ccccc2)c2ccccc2)cc1]

In one or more embodiments, the luminescent hybrid nanomaterial may comprise a restricted intramolecular rotation of the second substituent with respect to the first cyclic conjugated substituent. For example, in one or more embodiments, the second substituent 2, which is conjugated with the first cyclic conjugated substituent 1, may comprise a first carbon and a second carbon, the first carbon being bound to the first cyclic conjugated substituent (optionally through the linking moiety) and forming a first double bond with the second carbon as shown in FIG. 13.

Figure 13:
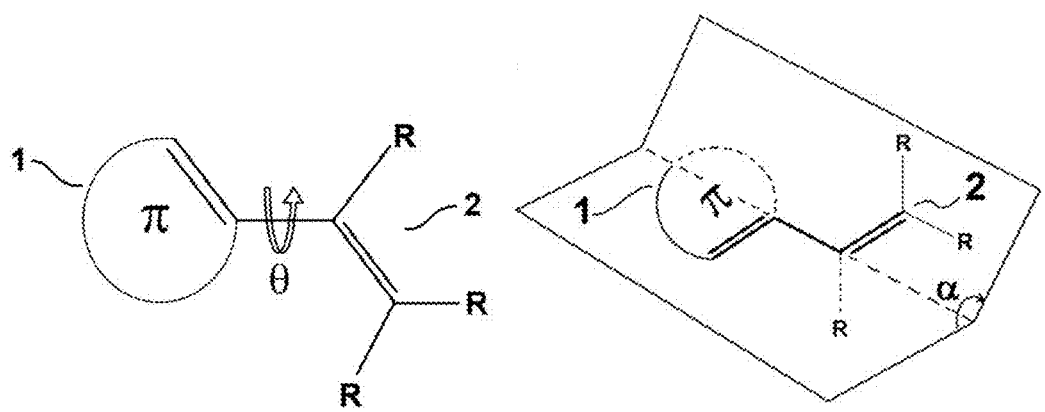
FIG. 13 shows a view of a luminescent hybrid nanomaterial that may comprise a restricted intramolecular rotation of the second substituent with respect to the first cyclic conjugated substitutent.

In accordance with one or more embodiments, FIG. 13 shows that the second substituent is conjugated (e.g. π- or σ-π-conjugated) to the first cyclic conjugated substituent and wherein the second substituent has a restricted intramolecular rotation with respect to the first cyclic conjugated substituent. Advantageously, in this way, emission of the second compound may be enhanced when grafted on the inorganic nanomaterial. Indeed, the Applicants have found that intramolecular rotation of the second substituent may be restricted with respect to the first cyclic conjugated substituent. In one or more embodiments, restriction of intramolecular rotation may be formed by 1/intramolecular interaction, for example due to steric and/or electronic constrains within the first and/or second substituent and/or 2/intermolecular interaction, for example due to steric and/or electronic constrains within a neighboring second compound also grafted on the inorganic nanomaterial, thereby blocking non-radiative decays and enhancing optical emission of the luminescent hybrid nanomaterial.

In the following, it is meant by "restriction of intramolecular rotation" the fact that a second substituent is not free to rotate at 360° within the conjugated system with respect to the first cyclic conjugated substituent. For example, the atom-atom bond, e.g. carbon-carbon bond, linking the first cyclic conjugated substituent and the second substituent may have a restricted rotation angle θ (e.g. θ<360°) at room temperature. For example, a dihedral angle α other than 180° between the plane of the first cyclic conjugated substituent and the axe of the first double bond may be present at room temperature. For example, the first cyclic conjugated substituent and/or the second substituent may comprise additional substituent(s), such as bulky groups, which may be configured to restrict intramolecular rotation.

In one or more embodiments, the intramolecular rotation may be unrestricted before grafting the second compound to the inorganic first compound of the inorganic nanomaterial. In alternative embodiments, the second organic compound may have restriction of intramolecular rotation before grafting. However, according to these alternative embodiments, the restriction of intramolecular rotation may further be restricted when grafted on the inorganic first compound.

In one or more embodiments, the first cyclic conjugated substituent and/or the second substituent may comprise a heteroatom such as, for example, a phosphorus atom thereby allowing modulation of electronic properties (emission wavelength, redox potential, etc.) of the luminescent hybrid nanomaterial. For example, the Applicants have found that the use of a heteroatom, particularly on the first cyclic conjugated substituent, may enhance emission properties of the luminescent hybrid nanomaterial of the present disclosure. For example, in one or more embodiments the first cyclic conjugated substituent may be a 5-member conjugated cyclic ring such as a heterole (e.g. phosphole, silole, etc.).

The incorporation of heteroatoms into conjugated frameworks is a very fruitful approach to provide new electronic and geometric properties. For example, molecular systems incorporating phosphorus atoms allows establishing structure-properties relationships revealing that heteroatom containing π-conjugated frameworks may provide excellent building blocks for the construction of π-conjugated systems with low HOMO-LUMO gap, which may be used as active organic materials in OLEDs. The presence of a phosphorus atom in P-containing emitting materials limits their aggregation and increases the efficiency of the OLED devices.

In one or more embodiments, the at least one inorganic nanomaterial may be selected from the group comprising a nanoparticle, a nanostructure and a material having a surface area to volume ratio greater than about 6 $\mu m^{-1}$.

In one or more embodiments, the at least one inorganic nanomaterial may comprise at least one length ranging from 1 nm to about 1 µm.

In one or more embodiments, the at least one inorganic nanomaterial may comprise a one-, two- or three-dimensional shape selected from the group comprising a nanosphere, nanorod, nanowires, nano-tetrapods, nano-multipods, nanocone, nanopyramide, and nanotriangle.

In one or more embodiments, the at least one inorganic nanomaterial may be selected from the group comprising semiconductors, metals and isolators.

In one or more embodiments, the at least one inorganic nanomaterial may comprise or consist of nanostructured or nanoporous substrates or electrodes.

In one or more embodiments, the at least one inorganic nanomaterial may be a nanoparticle having an average particle size of about 1 nm to about 1 µm.

In one or more embodiments, the at least one inorganic nanomaterial may comprise at least one inorganic compound (herein referred as the inorganic first compound) or consist of at least one inorganic compound.

In one or more embodiments, the inorganic first compound may comprise a metal selected from the group comprising alkali metals, alkaline earth metals, transition metals, post-transition metals, lanthanides, and metalloids.

In one or more embodiments, the inorganic first compound may comprise at least one metal oxide.

In one or more embodiments, the inorganic first compound may comprise a metal oxide selected from the group comprising a ZnO, SnO, ITO (indium doped tin oxide), FTO (fluoride doped tin oxide), $TiO_2$, $WO_3$, CuO and iron oxides. For example, the inorganic first compound may comprise or be ZnO.

Inorganic nanoparticles according to the present disclosure may have an average particle size lower than about 200 nm, preferably lower than about 100 nm and more preferably lower than about 50 nm. For example, Inorganic nanoparticles according to the present disclosure may have an average particle size ranging from about 1 nm to about 50 nm. Inorganic nanoparticles according to the present disclosure may be of different shapes such as sphere, rods or multipods. For example, a rod according to the present disclosure may have a diameter ranging from about 1 nm to about 50 nm and a length lower than about 100 nm (e.g. from 10 nm to 100 nm). Further, luminescent hybrid nanomaterials according to the present disclosure may comprise aggregates/clusters of inorganic nanoparticles. For example, said aggregates/clusters may have an average particle size ranging from about 10 nm to about 100 nm.

A nanomaterial according to the present disclosure may be a nanostructure or a material having a large surface area to volume ratio such as greater than about 6 $\mu m^{-1}$, preferably higher than 30 $\mu m^{-1}$. For example, a nanomaterial according to the present may be a material having a nanoporous structure and having a surface area to volume ratio greater than about 30 $\mu m^{-1}$. For example, a nanostructured substrate, made from deposited and sintered nanorods on the substrate, and having a surface area to volume ratio greater than about 30 $\mu m^{-1}$, may be a nanomaterial according to the present disclosure.

The average particle size of the inorganic compound according to the present disclosure may be measured by X-rays powder diffraction, for example. The X-rays powder diffraction involves a method described in the paper: Physical Review Letters 56 (1939), 978-982. The average particle size, obtained from the X-ray diffraction pattern, may be measured from the broadening of the peaks. According to one or more embodiments, the standard deviation of the particle size of the inorganic nanoparticles may be lower than about 20%.

Furthermore, a luminescent hybrid nanomaterial according to the present disclosure may be provided by a process of manufacture comprising: providing the at least one inorganic nanomaterial comprising the inorganic first compound; providing the at least one second compound; contacting the at least one second compound to at least part of the surface of the inorganic first compound, optionally in a solvent, under conditions appropriate to graft or physisorb the at least one second compound on the surface of the inorganic first compound thereby forming the luminescent hybrid nanomaterial; optionally isolating the luminescent hybrid nanomaterial; and optionally purifying the luminescent hybrid nanomaterial in a suitable solvent dissolving ungrafted molecules. Conditions appropriate to graft the at least one luminescent organic compound on the at least one inorganic nanoparticle may be a temperature and a pressure compatible with a solution process. Further, the second compound may be allowed to be grafted on the inorganic first compound for about an hour or less, or for more than an hour. Advantageously, the luminescent hybrid nanomaterials according to the present disclosure are stable for at least weeks in solution such as in chloroform and in a solid form such as when deposited on a thin film.

Furthermore, to provide luminescent hybrid nanomaterials according to the present disclosure, many modifications may be made on the second compound. For example, emission at a particular wavelength may be provided by adding/removing heteroatoms, donating substituents (e.g. —NR'''$_2$, NHR''', —NH$_2$, —OH, —OR, —NHC(O)R''', —OC(O)R''', R''', wherein R''' is an hydrocarbon, for example, as described for R2 to R6 or R8 to R10; for example, R''' may be a C1-C20 alkyl group), withdrawing substituents (e.g. —Z, —C(O)H, —C(O)R''', —C(O)OR''', —COOH, —C(O)Cl, —CF$_3$, —CN, SO$_3$H, —NH$_3^+$, —NR'$_3^+$, NO$_2$; wherein Z is a halogen and R''' is an hydrocarbon, for example, as described for R2 to R6 or R8 to R10; for example, R''' may be a C1-C20 alkyl group), and/or π-conjugated substituents (oligothiophene, fluorene, stilbene, etc., as described above) on the first cyclic conjugated substituent or the second substituent conjugated with the first cyclic conjugated substituent. Also, length of the first and/or second linkers as well as affinity of the anchoring groups/moieties with respect to the inorganic nanomaterial may also be modified to enhance emission properties of the luminescent hybrid nanomaterial. In addition, the non-planarity of the exemplary first double bound and the torsion angle may be modified by adding at least one sterically-hindering/bulky group, such as cyclic or branched, saturated or unsaturated, C3-C20 alkyl group (e.g. iPr, iBu, tBu, Ph, etc.), to at least one of the R2-R6 and R8-R10 substituents. Furthermore, the emission may also be changed by varying the type and/or number of second and/or third substituents.

By combining inorganic nanomaterials and second compounds according to the present disclosure, it is provided herein a synergy between the physicochemical properties of the inorganic nanomaterials and the physicochemical properties of the second compounds through the formation of the luminescent hybrid nanomaterial with enhanced emission properties. As a result, new efficient materials may be prepared for various applications in microelectronics (light-emitting hybrid diodes, OFET, etc.), for the detection of chemicals, and/or in a biological medium. For example, the synergetic combination of heteroles, e.g. phospholes and siloles, and inorganic nanomaterials, such as ZnO nanoparticle, provides tremendous emission improvement compared to a mere addition of the emission of the second compound and the emission of the inorganic nanomaterial.

In one or more embodiments, second substituents, such as at any one of positions R2 to R6 or R8 to R10, may advantageously repel the inorganic nanomaterial and limit the energy and/or electron transfer process between the inorganic nanoparticle and the luminescent organic compound. As a result, grafting to inorganic nanomaterial of other conjugated systems (e.g. additional compounds comprising different aggregation-induced emission moieties), which may be intimately-coordinate to nanoparticle surface, is possible.

In addition, according to the present disclosure, aggregation of adjacent inorganic nanomaterials, which comprise luminescent organic compound at their respective inorganic first compound surfaces, may also lead to a further increase in emission. For example, restriction of intramolecular rotation of the second substituent may further be enhanced by interaction with a second compound located at inorganic first compound surface of a neighboring inorganic nanomaterial. Thus, according to one or more embodiments, luminescent hybrid nanomaterial may show a two-step emission enhancement. Not only the emission intensity may be improved by varying the ratio between the number of inorganic nanomaterials and the number of second compounds, but also the emission intensity may be enhanced by changing the ratio between the inorganic nanomaterial and the second compound. In the same manner, the emission intensity may be enhanced by modifying the concentrations of the inorganic nanomaterial and the second compound.

Also, a hybrid nanomaterial according to the present disclosure may have semiconducting, photoswitchable and/or self-assembly properties. Also, thin films, luminescent solar concentrators, a light-emitting hybrid diodes and/or light-emitting hybrid field-effect transistors comprising a luminescent hybrid nanomaterial according to the present disclosure may be provided. Indeed, a luminescent hybrid nanomaterial according to the present disclosure may be used to manufacture a product selected from the group comprising a thin film, a luminescent solar concentrator, a light-emitting hybrid diode and a light-emitting hybrid field-effect transistor. For example, the luminescent hybrid nanomaterials according to the present disclosure can be further used to manufacture Light-emitting hybrid diode (HLED).

In one or more embodiments, a light-emitting hybrid diode (HLED) may comprise a substrate (e.g. glass, plastic substrates such as polyethylene terephthalate (PET) and polyethylene naphthalate (PEN) substrates, paper etc.); a transparent first electrode deposited on the substrate; an electron blocking layer (or a hole blocking layer) deposited on the transparent first electrode; a luminescent hybrid nanomaterial according to the present disclosure deposited on the electron blocking layer (or the hole blocking layer); a hole blocking layer (or an electron blocking layer) deposited on the luminescent hybrid nanomaterials; and a second electrode deposited on the hole blocking layer (or the electron blocking layer). In one or more embodiments of the present disclosure, depositing a layer may comprise annealing the layer, such as at a temperature ranging from about 280-360° C.

As a further example of applications, the luminescent hybrid nanomaterials according to the present disclosure may also be used to manufacture nanostructured electrodes such as a nanostructure cathode. In one or more embodiments, a nanostructured electrode may comprise a substrate (e.g. glass); a transparent electrode (e.g. ITO) deposited on the substrate; and a luminescent hybrid nanomaterial according to the present disclosure deposited on the transparent electrode. In one or more embodiments, as shown in FIGS. 7b-c, luminescent hybrid nanomaterials may be obtained via a grafting process of the second compound onto the surface of a nanostructured inorganic substrate (b) or inorganic nanoporous substrate (c). For example, the luminescent hybrid nanomaterial may have a nanoporous structure. A nanoporous structure may be formed, for example, by depositing a nanoporous layer of the inorganic nanomaterial in the form of nanorods, as shown in FIG. 7c. For example, such nanostructured electrode may allow the manufacture of further devices such as HLEDs using a "Grätzel cell" technique based on grafting of organic compounds onto nanoporous electrodes as described in, for example, Photoelectrochemical cells, Michael Grätzel, Nature 414, 338-344; and Solid-state dye-sensitized and bulk heterojunction solar cells using TiO2 and ZnO nanostructures: recent progress and new concepts at the borderline, J. Boucle, J. Ackermann, Polym. Int. (In Focus), (2012), 61, 355.

To resume, the luminescent hybrid nanomaterials according to the present disclosure may be provided with different shapes and sizes. Also, the luminescent hybrid nanomaterials according to the present disclosure show high emission intensity through grafting the second compound on the inorganic nanomaterial. Also, the luminescent hybrid nanomaterials according to the present disclosure may show even higher emission intensity through aggregation of adjacent inorganic nanomaterials. In short, when compared to organic nanoparticles, which are typically produced through complicated procedures and which show limited emission properties, the luminescent hybrid nanomaterial according to the present disclosure provide improved templates with not only enhanced emission properties but also stable morphology and optoelectronic properties.

EXAMPLES

In the following, the synthesis and physico-chemical analysis of exemplary second compounds and luminescent hybrid nanomaterials are provided. Also, the assembly and properties of exemplary luminescent hybrid nanomaterial are discussed.

Synthesis of Exemplary Second Compounds

First, three different phosphole molecules (S1-S3) were synthesized, as shown below:

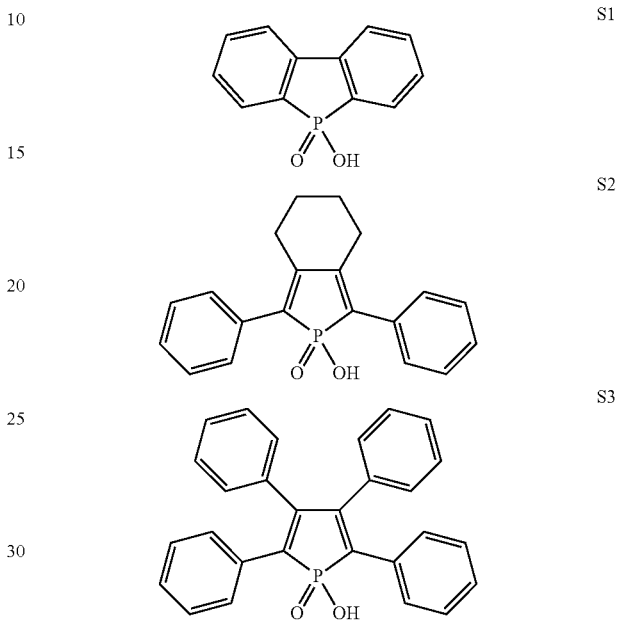

The synthesis of the organic fluorophores S1 (S1 being a comparative example), S2, S3 was made according to a modified published procedure based on the P—C bond cleavage of a $\sigma^3,\lambda^3$ phosphole in presence of alkali metal (see Phosphorus 1974, 4, 199-201). Starting from easily available P-derivatives, this method allow to obtain a fluorophore bearing the POOH function in moderate yield (≈50%). This synthetic strategy is exemplified on S3 in the following:

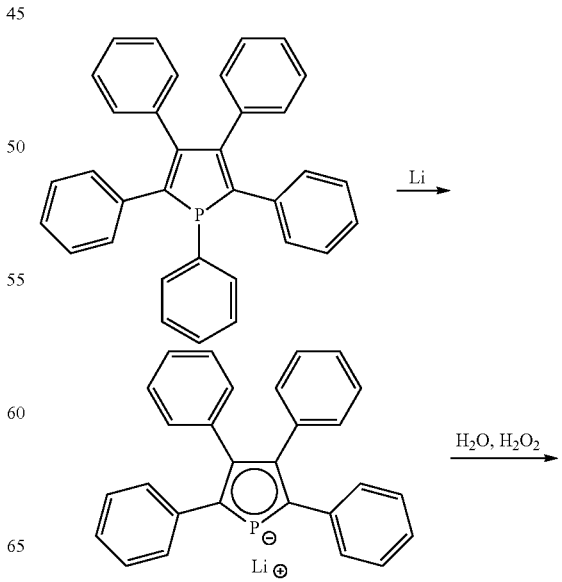

-continued

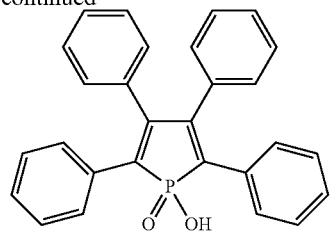

Figure 14:
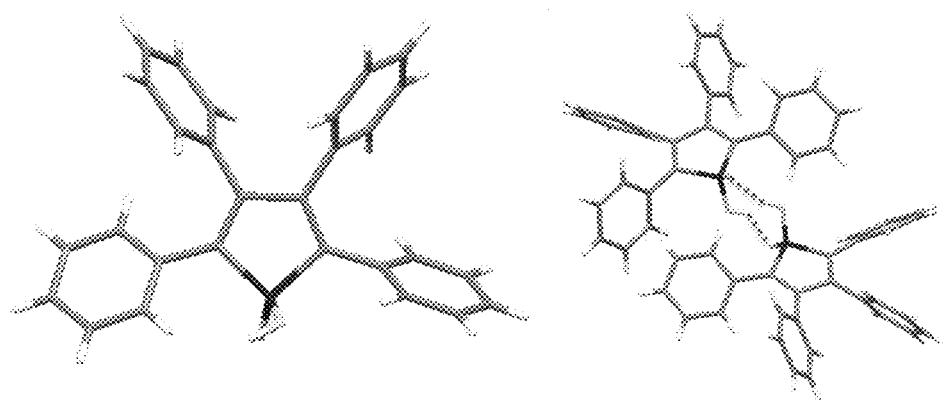
FIG. 14 shows views of the molecular structure as confirmed by X-ray diffraction study of monocrystals of the molecule.

The molecular structure of S3 was confirmed by X-ray diffraction study performed on monocrystals as shown in FIG. 14:

The bond length and angles in the phosphole moiety are classical for such compound. Interestingly, the lateral phenyl rings are deviated from planarity due to steric repulsion (dihedral angle≥30°). All these structural properties have been confirmed by DFT theoretical calculations performed at the DFT level (B3LYP/6-3l+g*). At the intermolecular level, molecules interact through H-bond between phosphoric acid moieties.

Exemplary Luminescent Hybrid Nanomaterials

Figure 4B:
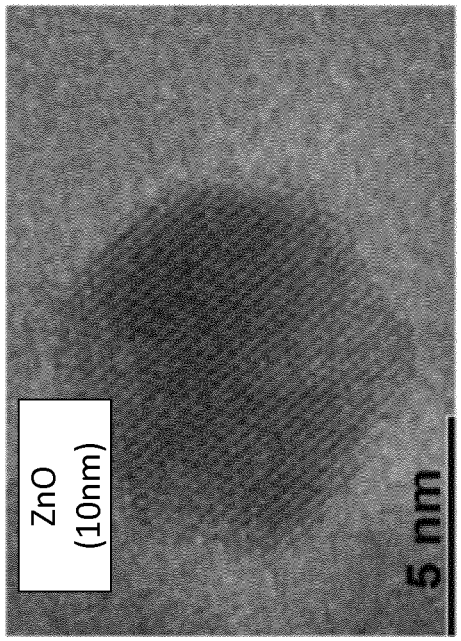
FIGS. 4a-c show transmission electron microscopy (TEM) images of inorganic nanomaterials according to the present disclosure.
Figure 4C:
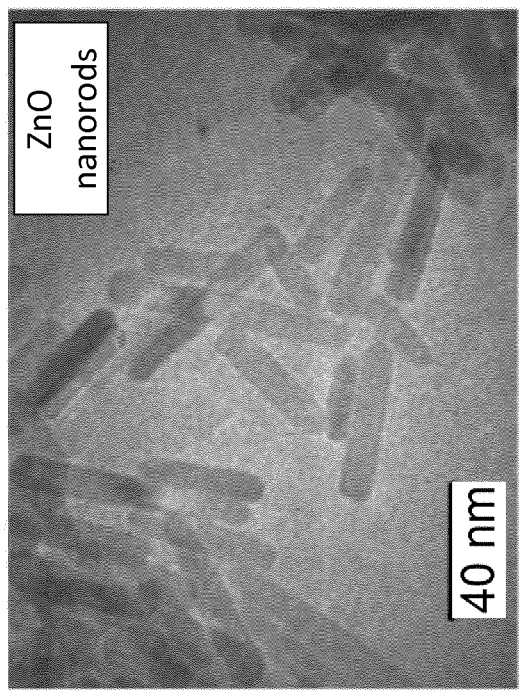
Figure 4A:
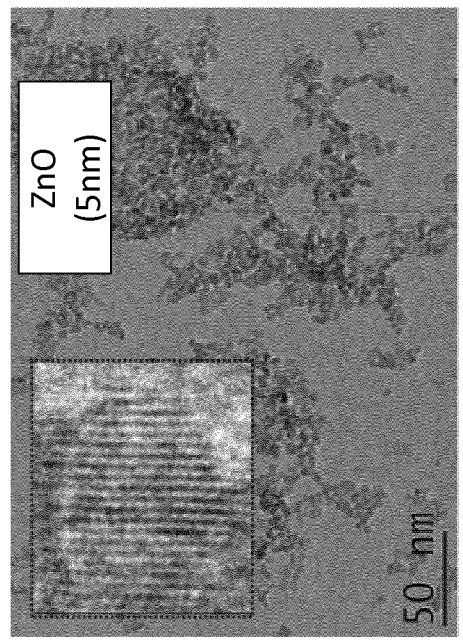
Figure 5A:
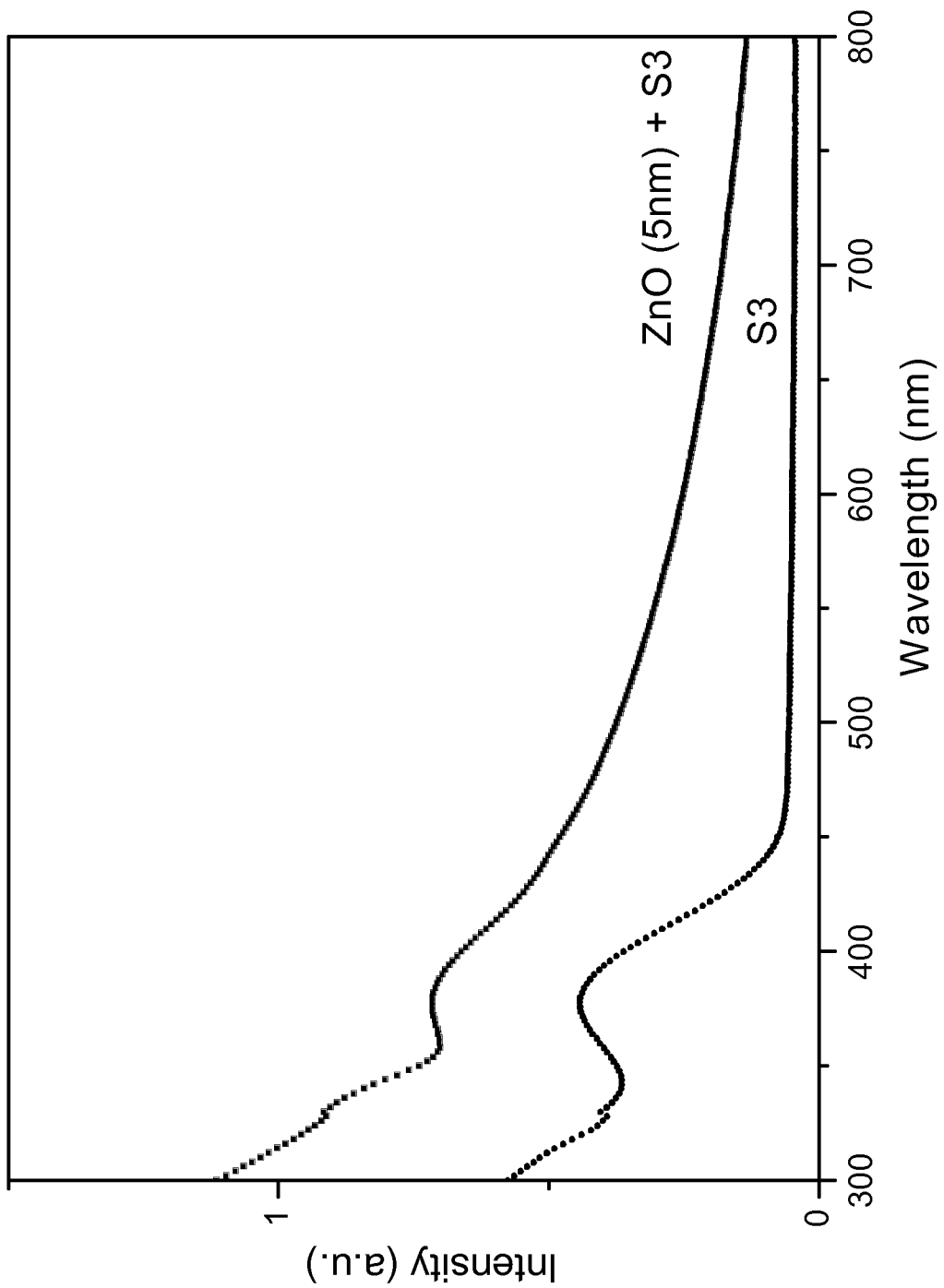
FIGS. 5a-f show absorbance (a-c) and fluorescence (d-f) spectra of luminescent hybrid nanomaterials according to the present disclosure.
Figure 5B:
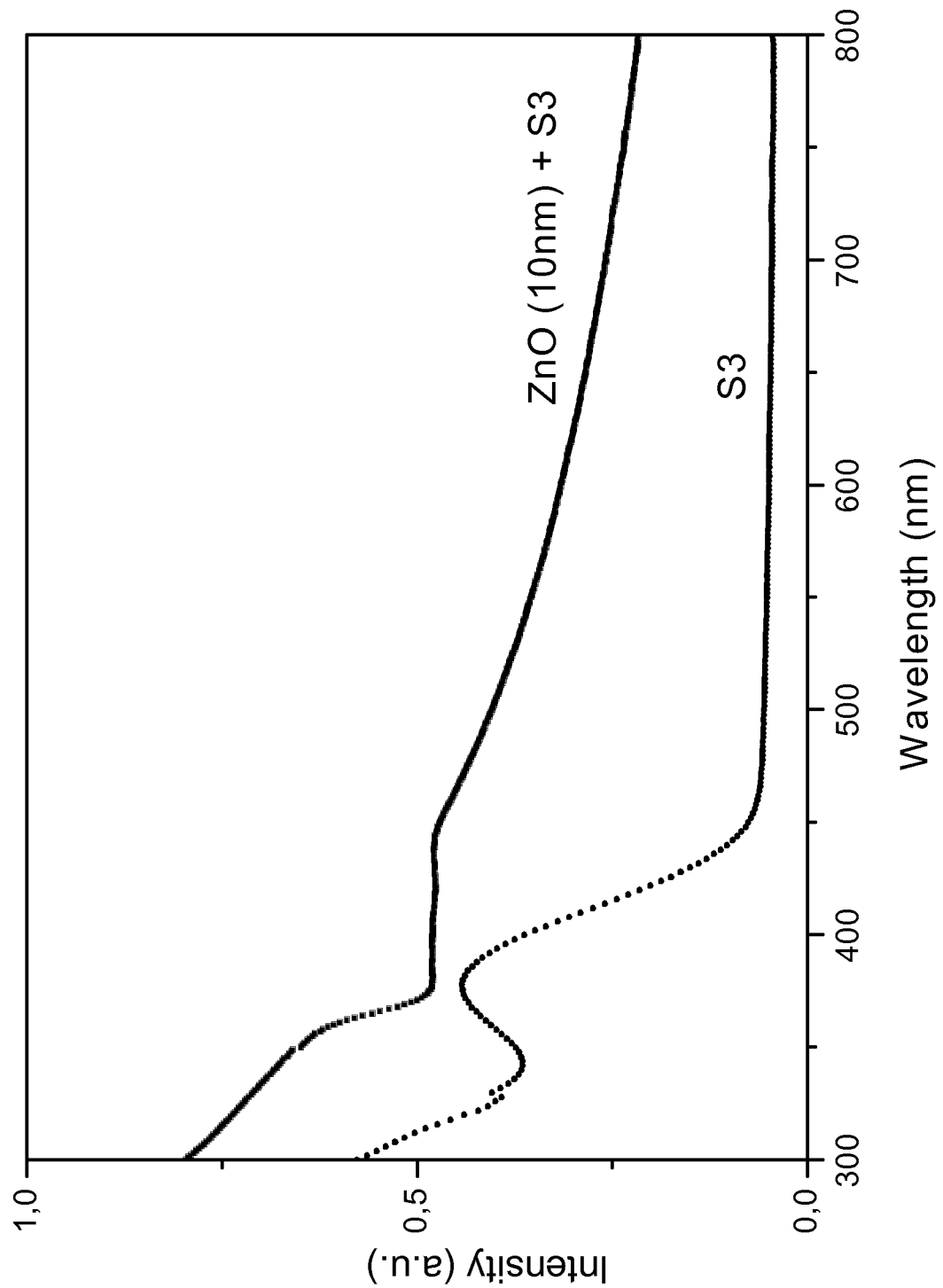
Figure 5C:
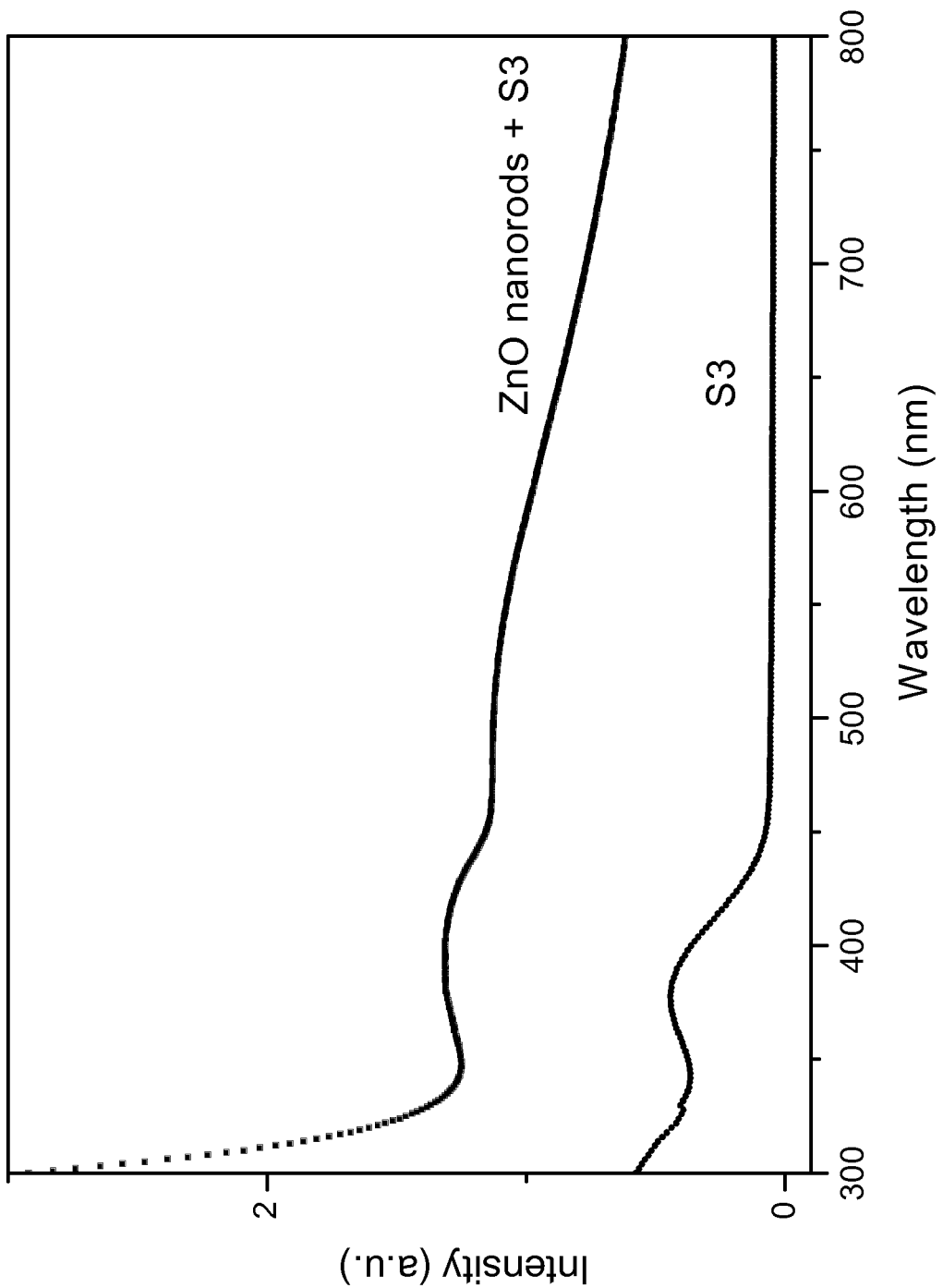
Figure 5D:
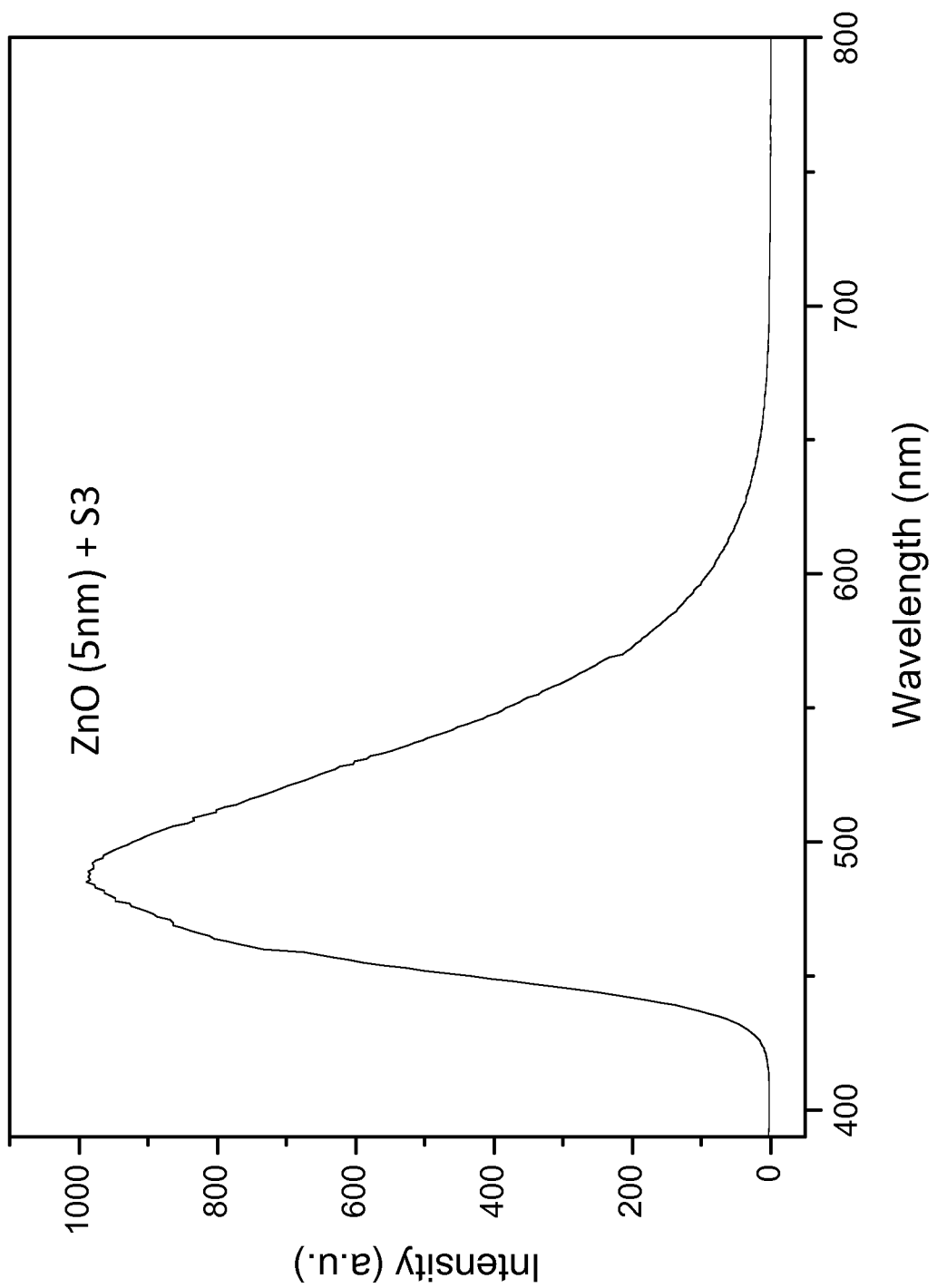
Figure 5E:
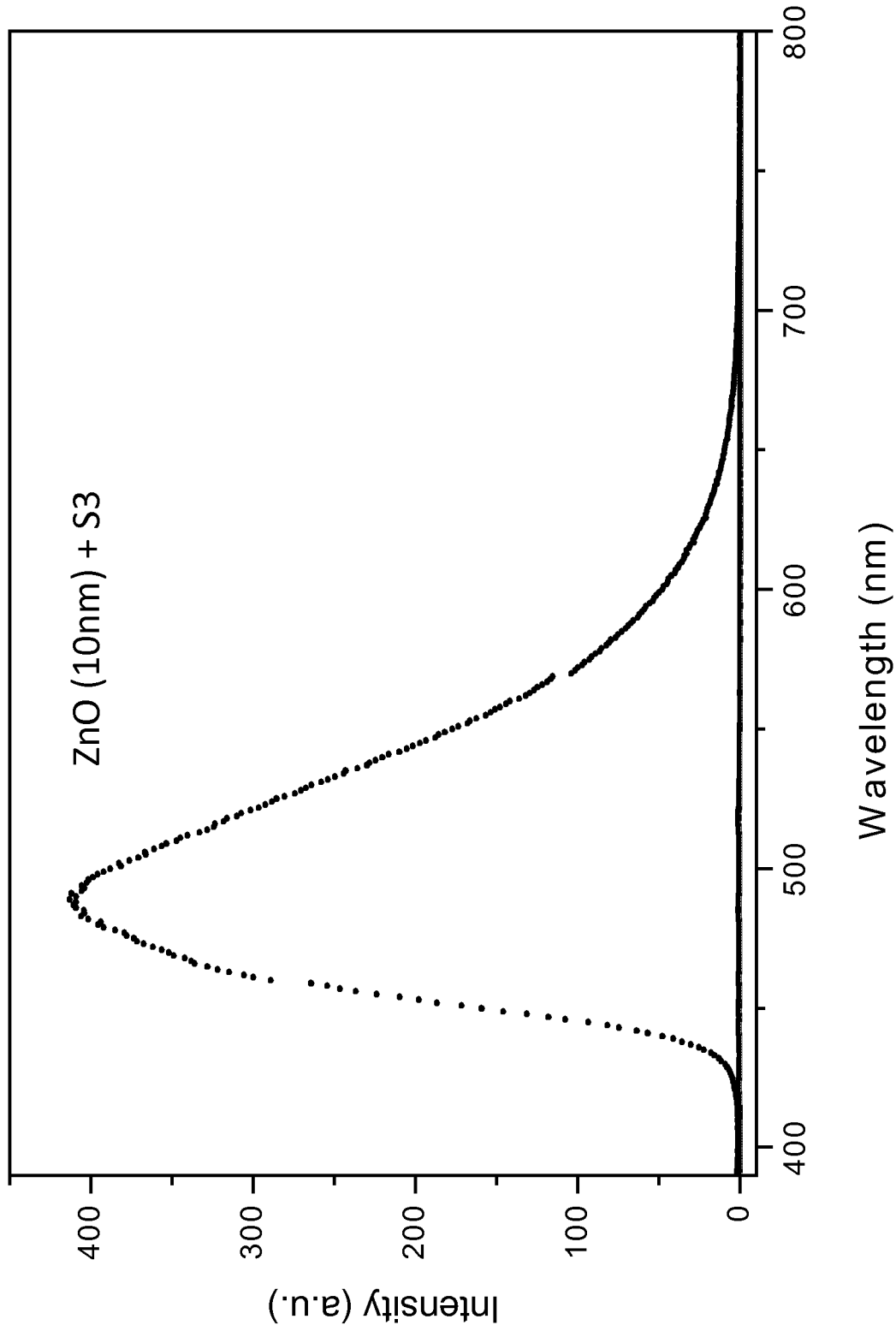
Figure 5F:
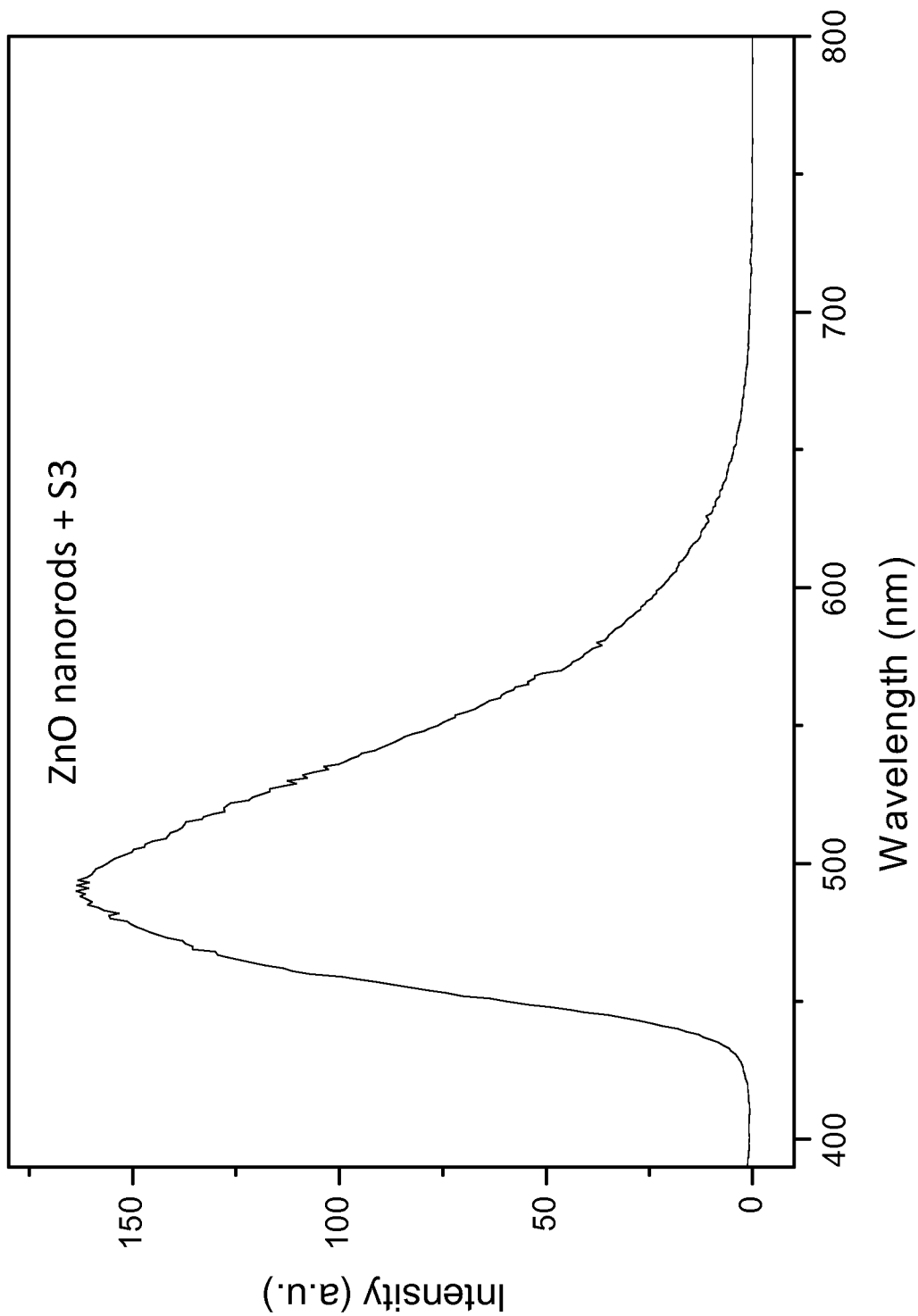

The Applicants have first investigated the S3 attachment on the surface of ZnO nanoparticles (5 nm or 10 nm). FIGS. 4*a*-*c* show transmission electron microscope (TEM) images of the ZnO used in this study (a: 5 nm; b: 10 nm; c: nanorods). Advantageously, ZnO nanoparticles may have different sizes and shape. In these examples, nanospheres have an average diameter of 5 nm or 10 nm, and nanorods NR have an average length of 45 nm and an average diameter of 10 nm. Molecule S3 was mixed with ZnO 5 nm or 10 nm in chloroform in order to assemble two hybrid nanosystems (i.e. nanohybrid; luminescent hybrid nanomaterials according to the present disclosure). FIGS. 5*a*-*f* show absorption (*a*-*c*) and fluorescence (*d*-*f*) of said nanosystems (a: ZnO 5 nm+S3; b: ZnO 10 nm+S3; c: ZnO nanorods+S3).

Spectra of ZnO—S3 nanohybrids using ZnO of 5 nm or 10 nm. First of all, the absorption spectra of S3 change after grafting indicating strong interaction with the ZnO nanoparticles. In the case of ZnO (10 nm) this is effect is more pronounced compared to ZnO (5 nm). Secondly, the absorption spectra of all ZnO—S3 nanohybrids show increased light scattering compared to S3 and ZnO alone, which indicates the formation of aggregates/clusters of nanohybrids. Third, the Applicants observed a strong green emission centered at 490 nm after excitation at 380 nm in the absorption maximum of the grafted molecule while S3 alone only shows weak emission. In both cases of ZnO emission enhancement is observed, while in the case of ZnO (5 nm) the effect is more pronounced and emission is amplified by several orders of magnitude.

Also, it may be seen that when S3 is added into the ZnO suspension, the second compound may induce aggregation of ZnO nanoparticles. For example, aggregates/clusters of around 200 nm of diameter may be formed. In the case of pure ZnO nanoparticles, no cluster was observed showing that the formation of clusters may be introduced by grafting second compound on the surface of the inorganic first compound.

Emission Studies of the Luminescent Hybrid Nanomaterial

First results on the nanohybrids reveal that S3 grafting on ZnO surface increases strongly light emission of S3. Further experiments were performed to describe whether the fluorescence enhancement arises from the grafted S3 and/or from the clustering of nanoparticles. Also, molecule S2 and S1 were synthesized in order to study the impact of the molecule structure on the fluorescence properties of the nanohybrids.

Figure 6A:
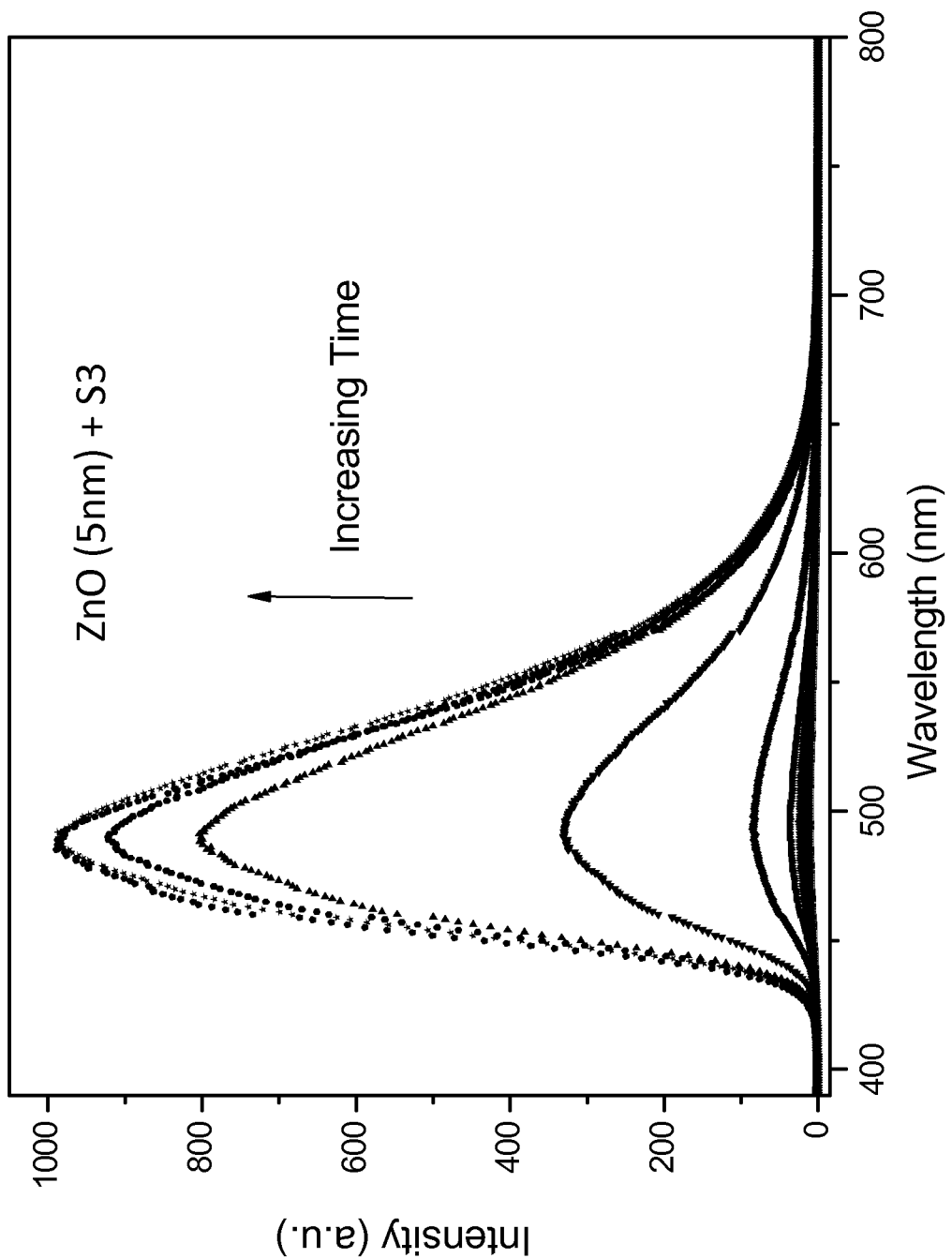
FIGS. 6a-b show time evolution of the emission intensity as adding the inorganic compound (ZnO nanospheres of 5 nm and 10 nm in diameter, respectively) to a chloroform solution containing second compounds according to the present disclosure.
Figure 6B:
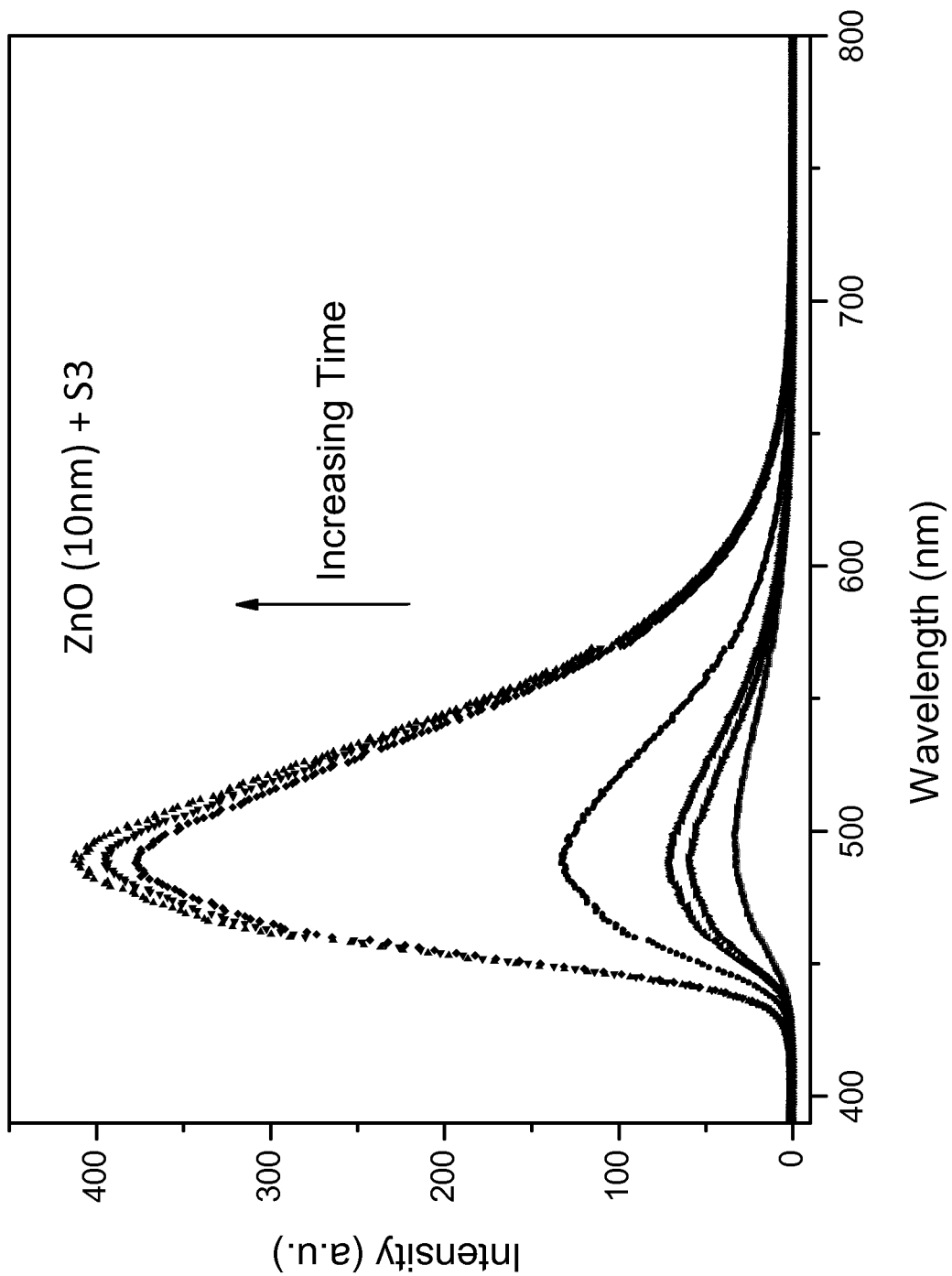

The emission intensity of $ZnO_{5nm}$-S3 was studied dynamically by recording emission spectra at different time (FIG. 6*a*). After adding $ZnO_{5nm}$ nanoparticles into the solution containing phosphole S3, the luminescence intensity gradually increased, from initial intensity at 7.5 to a final intensity of around 1000 in 30 minutes, which is a great intensity enhancement. An additional study showing similar results was also performed using $ZnO_{10nm}$-S3, as shown in FIG. 6*b*.

As the solutions of ZnO nanoparticles and of S3 are both very transparent in the visible, no aggregates are present in the respective solution. However, mixing both together may lead to the formation of aggregates as indicated by the increase in light scattering in solution. Thus, grafting of S3 to the surface of ZnO can induce aggregation, as shown in FIG. 7*a*, between nanohybrids leading to increase in fluorescence.

Figure 9A:
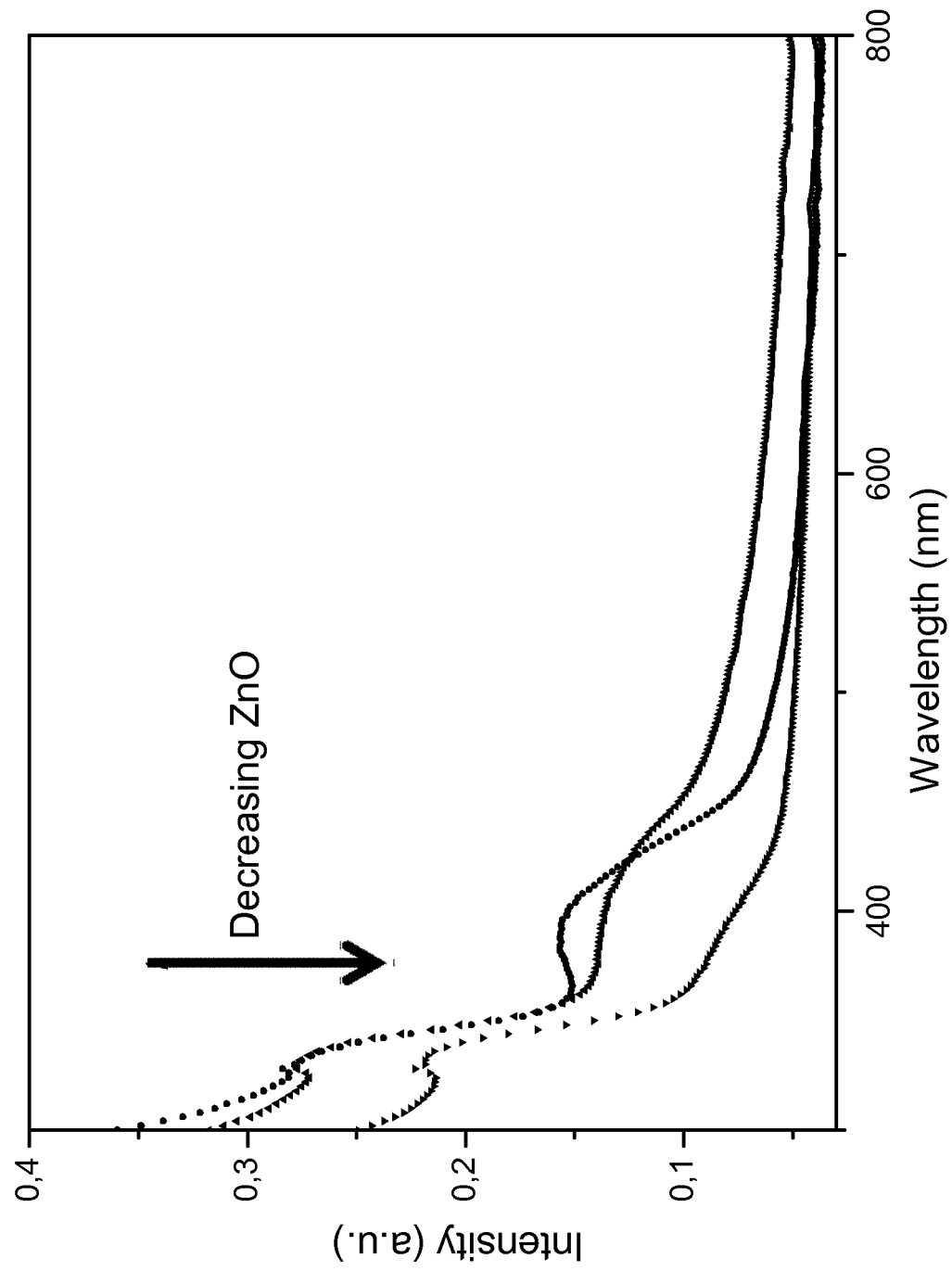
FIGS. 9a-b show absorption (a) and fluorescent (b) spectra of $ZnO_{5nm}$ nanoparticles grafted with a second compound S3 with decreasing concentration of ZnO.
Figure 9B:
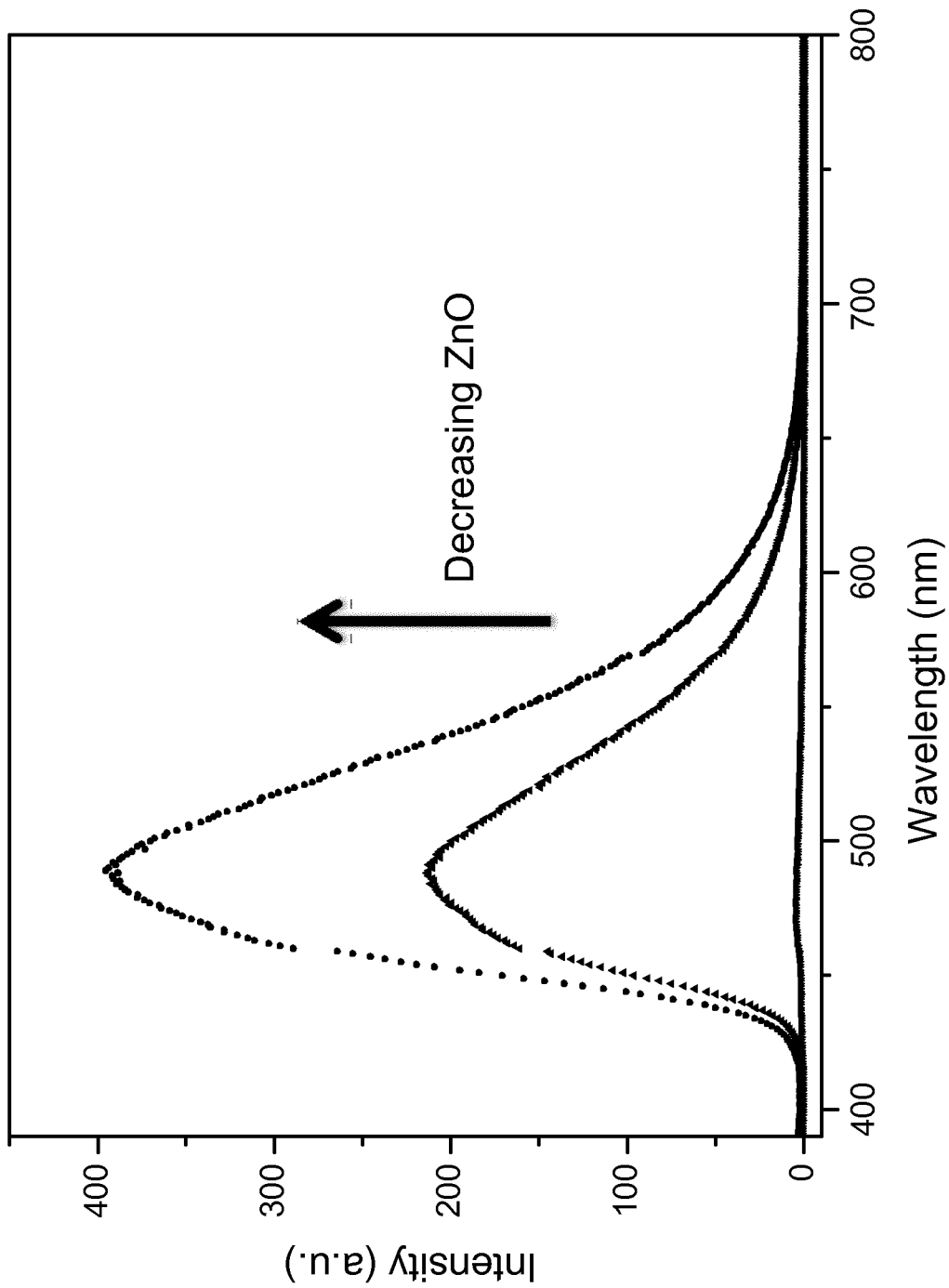
Figure 10B:
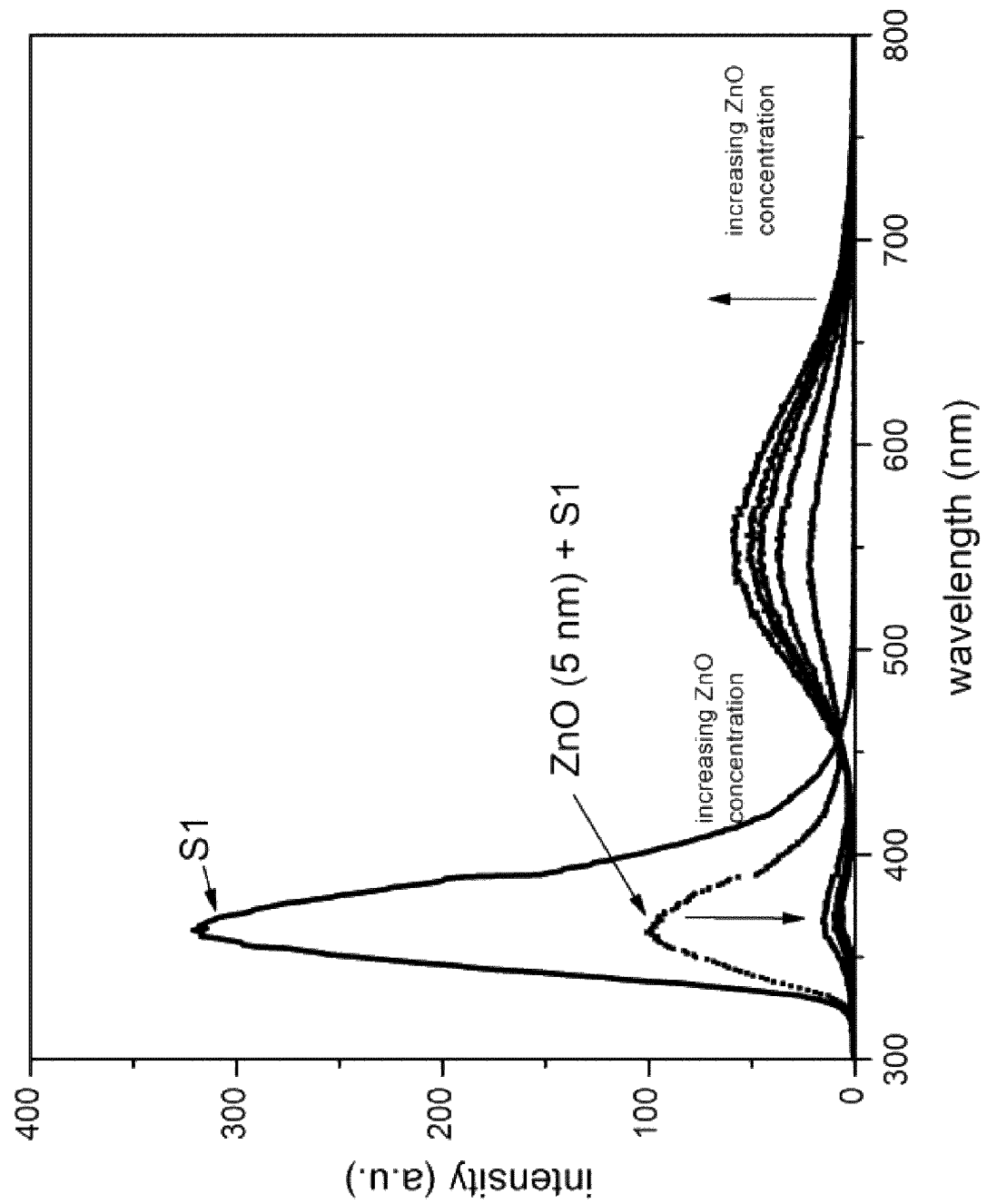

As a next step, different grafting techniques are compared in order to understand the origin of cluster formation. In the former case, such as presented in FIGS. 5*a* and 5*d*, S3 molecules were injected into ZnO solution, such as $ZnO_{5nm}$. In the new experiments, nanohybrids prepared by injecting ZnO nanoparticles into S3 solution were studied. Different concentrations of ZnO were used. The applicants found that in this case of inverted injection order, no additional light scattering could be observed in the absorption spectra compared to the ZnO nanoparticle solution and aggregate size of ZnO nanoparticles was not increased, while the luminescence intensity was increased compared to ungrafted S3 molecules indicating clearly that S3 emission increase is due to grafting of S3 onto individual nanoparticles. However total emission was found lower than in the case of cluster formation demonstrating that cluster formation may further increase the luminescence intensity of the grafted compound. The applicants further found that the emission intensity is largely enhanced for the lowest concentration of ZnO compared to S3 alone, while further increase in ZnO concentration may reduce emission to the level of the ungrafted molecules as it can be seen in FIGS. 9*a* and 9*b*. This behavior can be understood by taking into account that increasing the ZnO concentrations in the mixture reduces the average amount of grafted S3 molecules per ZnO nanoparticle. As aggregation between S3 molecules is responsible for the increase in emission, in one or more embodiments, emission enhancement may depend on the concentration of grafted molecules and may lead to loss in emission for low S3 coverage at ZnO. From these experiments, the Applicants have found that cluster free $S3$-$ZnO_{5nm}$ nanohybrids may form and show strong emission enhancement. Furthermore, emission intensity can be enhanced by varying the concentrations and ratios of S3 at the surface of ZnO nanoparticles. Additionally, formation of cluster of nanohybrids may further increase the emission of the hybrid nanomaterials Further, the Applicants grafted molecules S1 and S2 on the surface of $ZnO_{5nm}$ in order to study the effect of the molecule structure on the emission properties of the corresponding nanohybrids. FIGS. 10*a*-*b* show the absorption and emission spectra of $S1$-$ZnO_{5nm}$ nanohybrids. Different concentrations of ZnO were used as before in the case of $S3$-$ZnO_{5nm}$. As it can be seen in FIG. 10*a*, the absorption spectra show an increase in light absorption in the UV due to the injection of ZnO nanoparticles with an absorption onset at 360 nm. The emission intensity of the pure S1 is high and gradually reduces when adding ZnO nanoparticles.

With more ZnO$_{5nm}$ added, only the emission intensity of the ZnO defects at 550 nm is gradually enhanced. The results reveal that grafting of S1 induces emission quenching which can be addressed to the aggregation amongst grafted molecules at the surface of the ZnO nanoparticles. This observation is in line with the fact that S1 has rigid and planar structure that forms stacking amongst S1 leading to aggregated caused quenching.

Figure 11A:
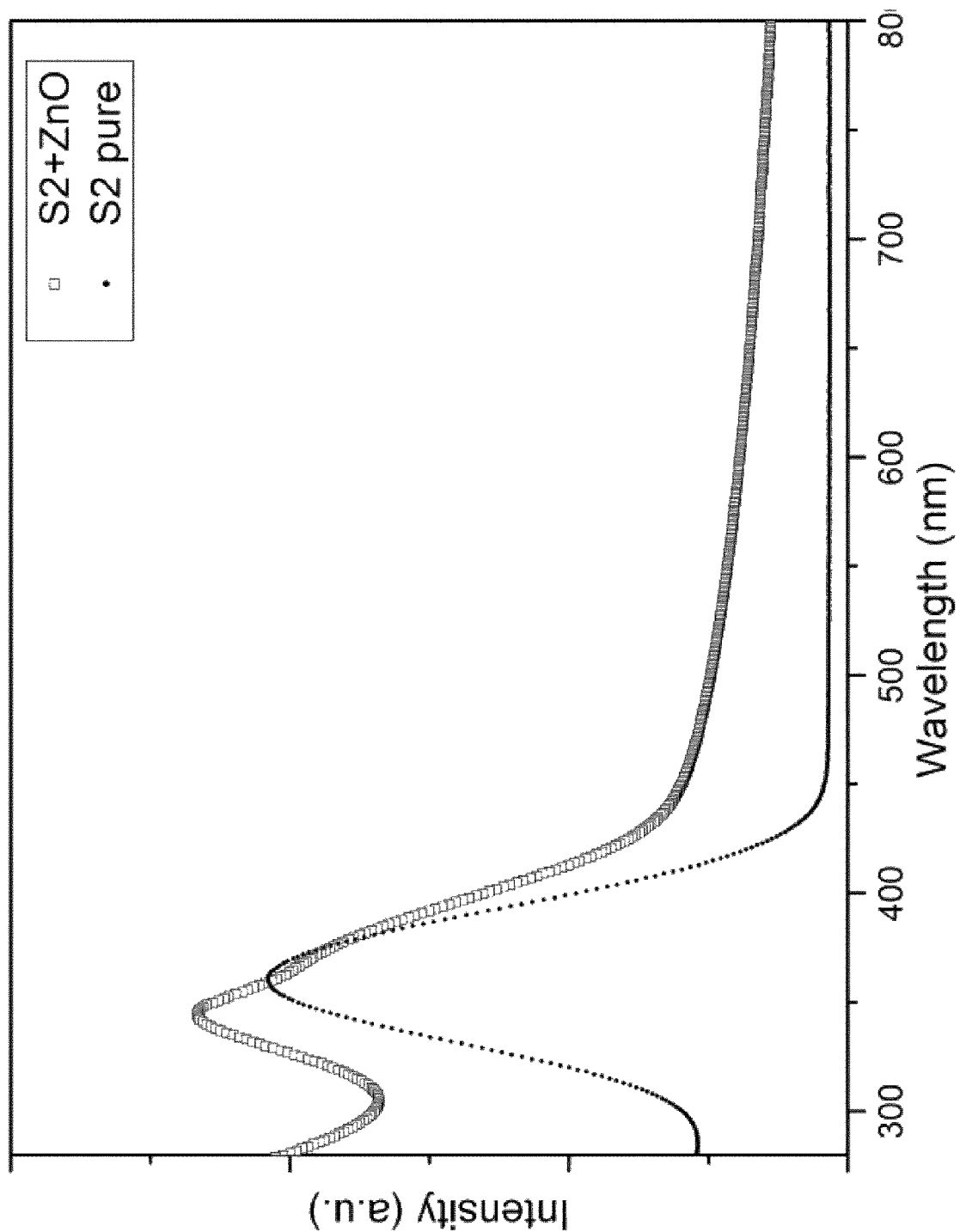
FIGS. 11a-b show absorption (a) and time evolution of the fluorescent (b) spectra of luminescent hybrid nanomaterials based on ZnO nanoparticles (5 nm) grafted with second compound S2 according to the present disclosure.
Figure 11B:
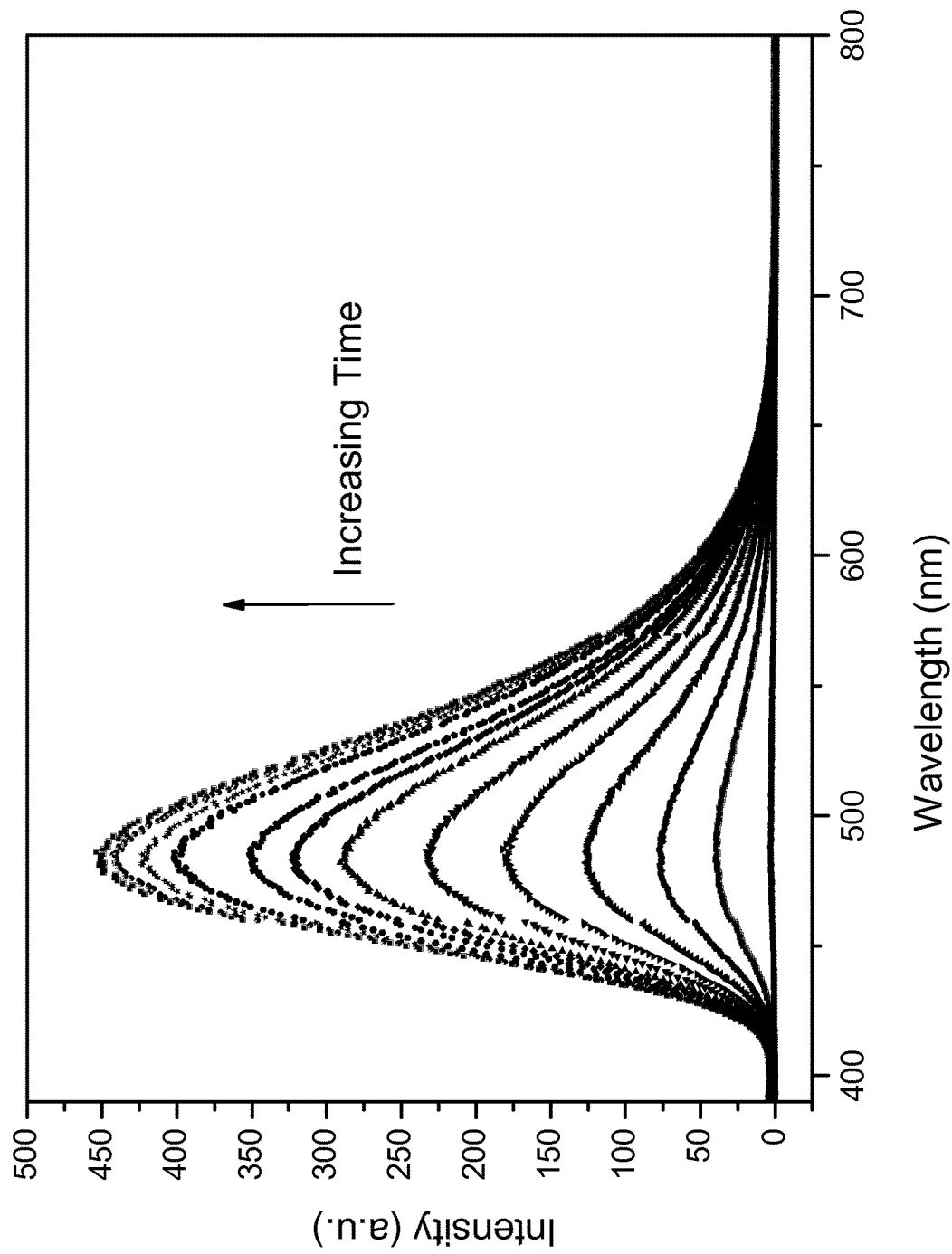

Further, the Applicants grafted S2 onto ZnO$_{5nm}$ to see whether enhanced emission properties are obtained compared to S1. FIGS. 11a-b show absorption and emission spectra of S2-ZnO$_{5nm}$. Here, the Applicants observe the same behavior as compared to S3 based nanohybrids. The emission intensity of S2-ZnO$_{5nm}$ is enhanced compared to the ungrafted molecule S2. Although, the effect is less pronounced compared to S3, this behavior indicates that the presence of phenyl group is important for the emission enhancement and their number inside of the compound may influence the emission intensity.

Figure 8A:
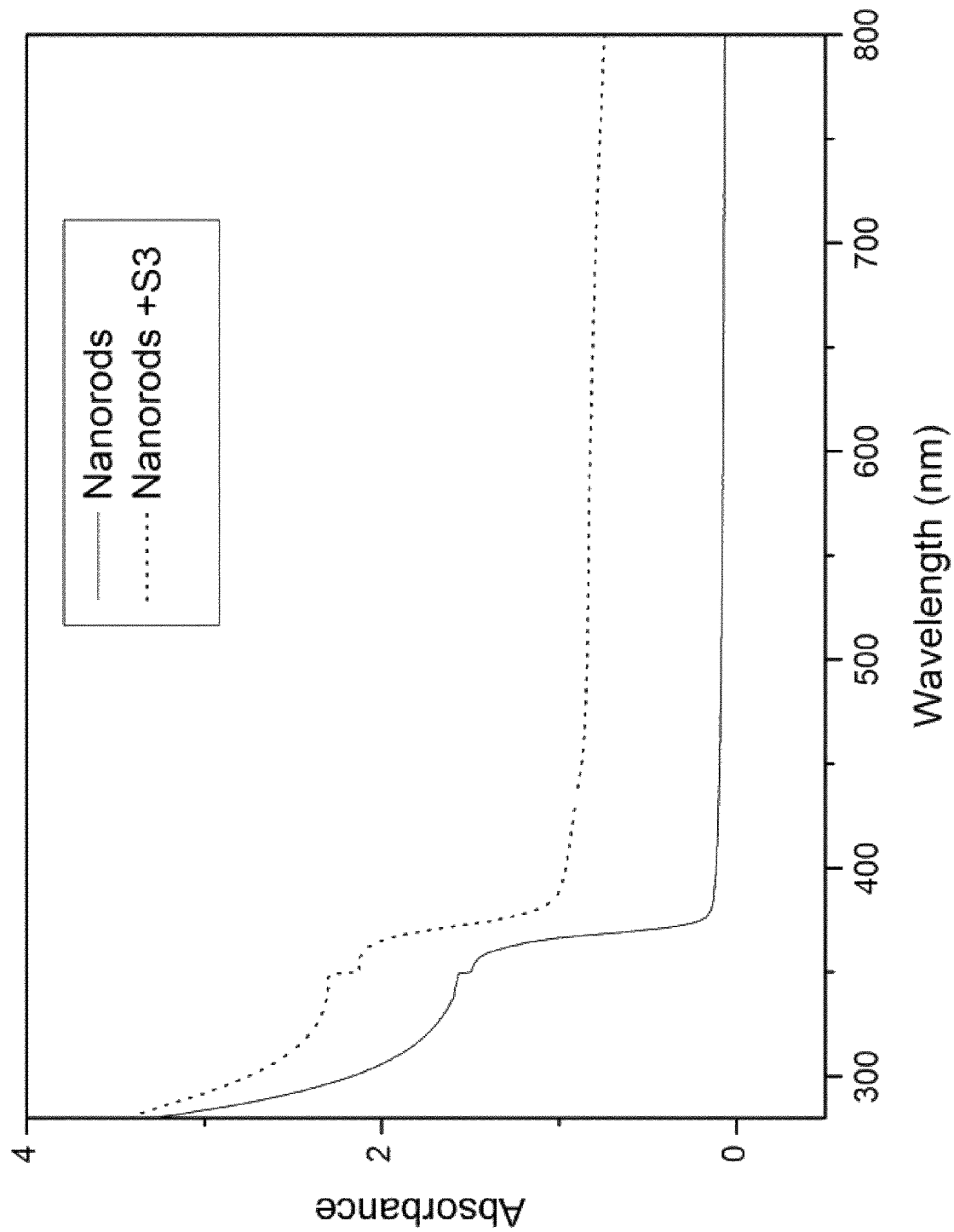
FIGS. 8a-b show the absorption spectra (a) and fluorescent spectra (b) of a fluorescent thin film based on a nanoporous substrate made by ZnO nanorods on an ITO substrates before and after grafting a second compound according to the present disclosure.
Figure 8B:
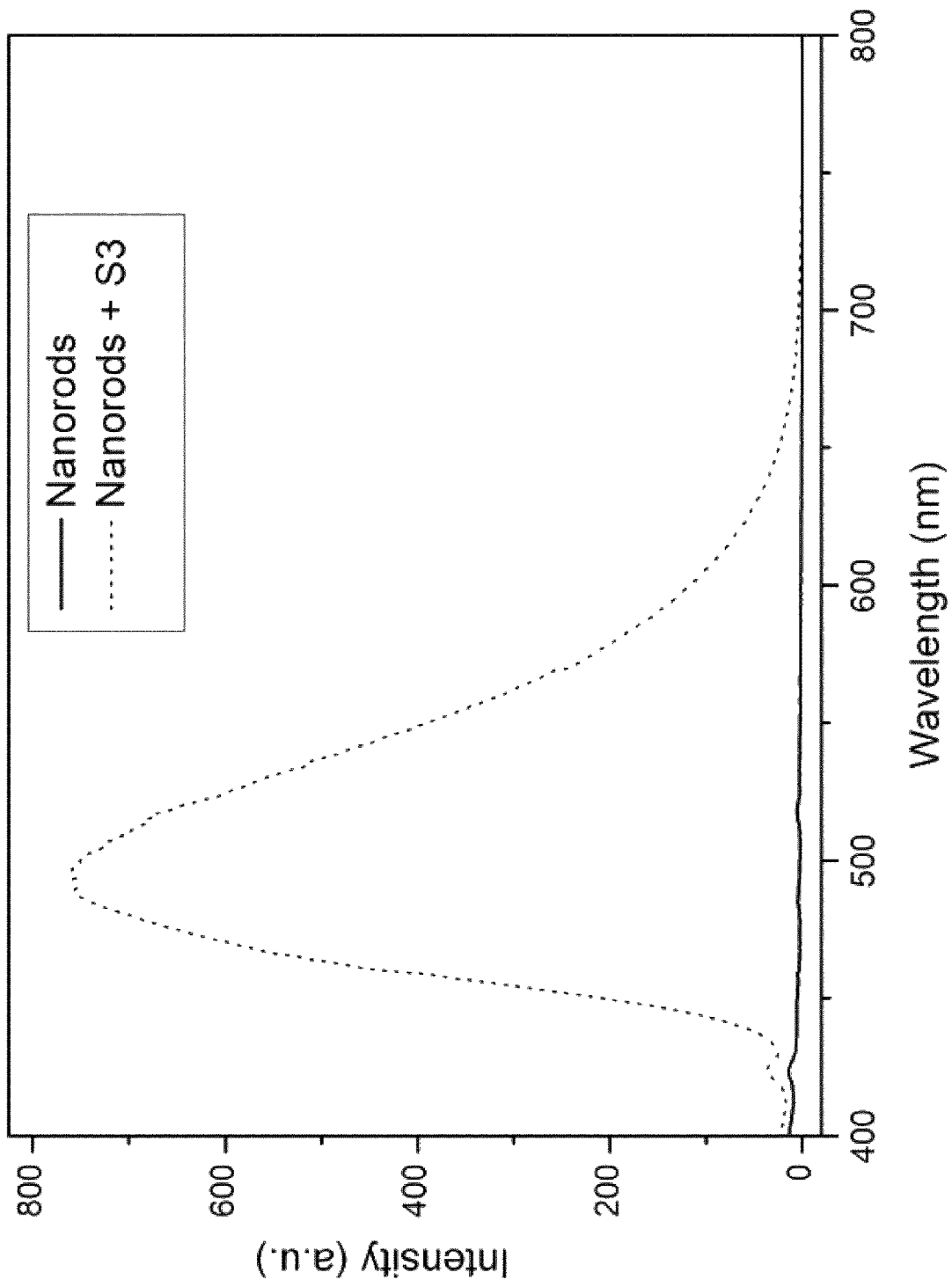
Figure 8E:
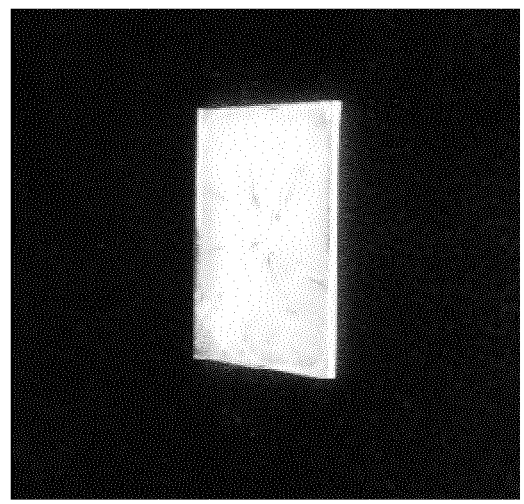
FIGS. 8c-e show the structure (c), and photos before (d) and after (e) illumination at 380 nm of a thin film based on luminescent hybrid nanomaterials according to the present disclosure; the light-emitting device being derived from the sensitized nanoporous substrate.
Figure 8D:
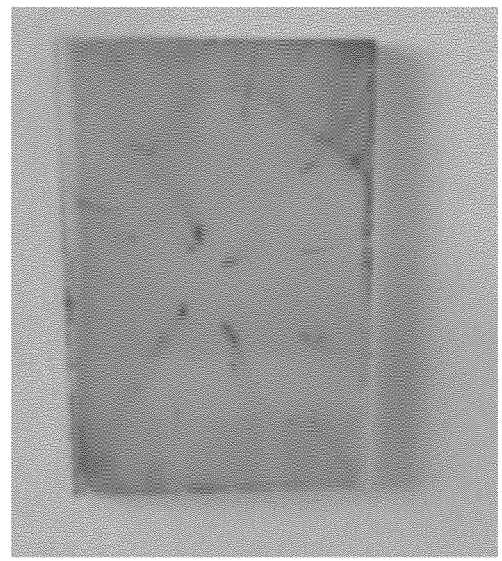

The grafting of S3 molecules was also applied to ZnO nanorods (NRs). Under the same condition, the S3 excitation and emission show identical features, but less in intensity (see FIGS. 5c and 5f). These observations indicate that the second compounds may be adapted to any morphology and shape of the inorganic nanomaterials without altering but rather enhancing emission properties of the resulting luminescent hybrid nanomaterials. In order to demonstrate the possibility to apply S3 to nanostructured substrates, the applicants prepared nanoporous ZnO layer on top of ITO via spin coating of first a dense ZnO$_{5nm}$ nanoparticle layer followed by a thick layer of ZnO nanorods that was annealed at 320° after deposition to form a nanoporous layer. Grafting of S3 onto this nanoporous materials lead to highly luminescence thin films in air. In FIGS. 8d-e, one can see the photos of such S3 grafted ZnO nanoporous film on ITO substrates that emit light strongly over the whole surface after excitation at 365 nm in air, as shown in FIG. 8b (respective absorption spectra shown in FIG. 8a).

Figure 8C:
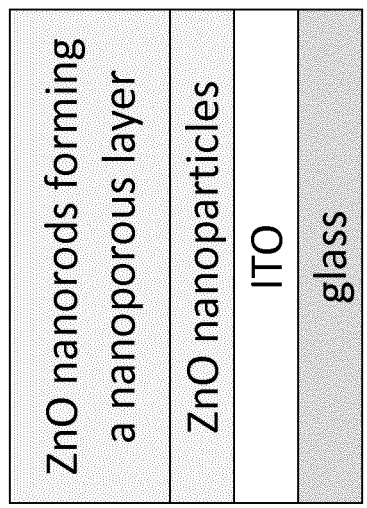
Figure 12B:
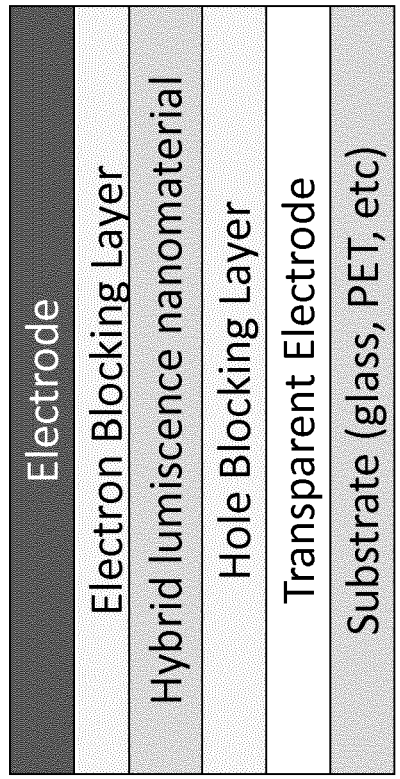
FIGS. 12a-b show device structures of hybrid light-emitting diode (HLED) using either a structure starting with an electron blocking (a) or a hole blocking layer (b) deposited onto the transparent electrode.
Figure 12A:
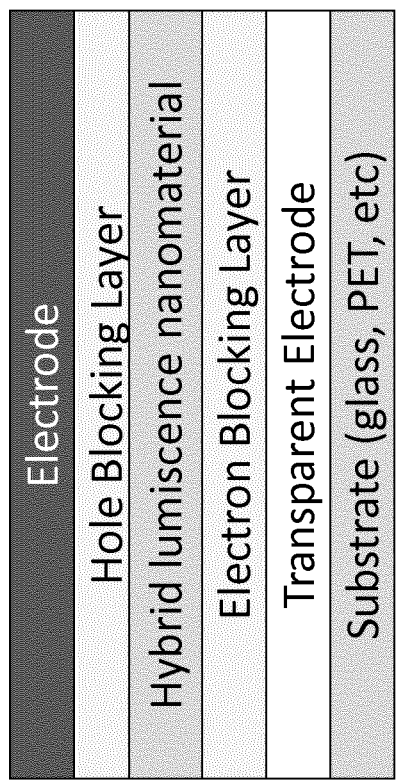

The luminescent hybrid nanomaterials according to the present disclosure can be further used to manufacture Light-emitting diode (LED). In contrast to organic LED, so called OLEDS, using the luminescence properties of the hybrid nanomaterial according to the present disclosure allow constructing hybrid LED (HLED) that opens new possibilities for device architectures. FIGS. 12a and 12b show device structures that can be processed using the hybrid nanomaterial as emissive layer. For example, the device structure may be manufactured by depositing an electron blocking (FIG. 12a) or a hole blocking layer (FIG. 12b) onto the transparent electrode. FIG. 8c shows the structure of a nanostructured cathode using nanoporous hybrid thin films. For example, the structure shown in FIG. 8c may allow the manufacture of a HLED, for example using a "Graetzel cell" technique, which is based on grafting of organic compounds onto nanoporous electrodes.

Furthermore, these exemplary embodiments confirm that the emission is mainly induced by restriction of intermolecular rotations. quantum efficiencies were also calculated using quinine bisulfate as standard and using the following equation for quantum yield determination:

$$\Phi = \Phi_R \times \frac{Int}{Int_R} \frac{1-10^{-A_R}}{1-10^{-A}} \frac{n^2}{n_R^2}$$

where $\Phi$ is the quantum yield, Int is the area under the emission peak (on a wavelength scale), A is absorbance (also called "optical density") at the excitation wavelength, and n is the refractive index of the solvent. In the equation above, the subscript R denotes the respective values of the reference substance.

The calculated quantum yield for S3 grafted on ZnO$_{5nm}$ nanoparticles has a typical value of 19%. This value is higher than the reported quantum efficiencies of related second compounds. According to the present disclosure, luminescent hybrid nanomaterial having a quantum yield greater than 10%, preferably greater than 15%, and more preferably greater than 20% may be obtained.

Concerning stability, the Applicants have found that exemplary S3-ZnO$_{5nm}$ samples show emission properties and morphologies, which are stable over weeks in chloroform solution. This makes them strongly improved in material properties compared to organic based nanoparticles (e.g. nanoparticles having organic molecules as the core of the nanoparticle) such as phosphole molecules, which show instability already in about a day or two.

Synthesis and analytical methods: Experiments were performed under an atmosphere of dry argon using standard Schlenk techniques. Commercially available reagents were used as received without further purification. Separations were performed by gravity column chromatography on basic alumina (Aldrich, Type 5016A, 150 mesh, 58 Å) or silica gel (Merck Geduran 60, 0.063-0.200 mm). $^1$H, $^{13}$C, and $^{31}$P NMR spectra were recorded on a Bruker AM400, AM500. $^1$H and $^{13}$C NMR chemical shifts were reported in parts per million (ppm) relative to Me$_4$Si as external standard. Assignment of proton and carbon atoms is based on COSY, HMBC, HMQC and DEPT-135 experiments. High-resolution mass spectra were obtained on a Varian MAT 311 or ZabSpec TOF Micromass instrument at CRMPO, University of Rennes 1. Elemental analyses were performed by the CRMPO, University of Rennes. UV-Visible spectra were recorded at room temperature on a VARIAN Cary 5000 spectrophotometer. The UV-Vis-N/R emission and excitation spectra measurements were recorded on a FL 920 Edimburgh Instrument equipped with a Hamamatsu R5509-73 photomultiplier for the NIR domain (300-1700 nm) and corrected for the response of the photomultiplier. Single crystal data collection were performed at 150 K with an APEX II Bruker-AXS (Centre de Diffractométrie, Université de Rennes 1, France) with Mo-Kα radiation (λ=0.71073 Å). Geometries were optimized at the B3LYP/6-31+G* level without any constraint using the Gaussian 09 suite of programs. Size and shape of ZnO nanoparticles were characterized by high-resolution transmission electron microscopy (HR-TEM) (JEOL 3010, acceleration voltage of 300 kV). UV-Vis absorption and fluorescence investigations were recorded using a Varian CARY 5000 spectrophotometer and a CARY Eclipse spectrometer, respectively.

Although the above-mentioned embodiments have been described in detail, it is understood that alternative embodiments of the disclosure can be envisaged. Thus, for example, inorganic first compounds other than ZnO may be used to provide a luminescent hybrid nanomaterial according to the present disclosure. In addition, various compositions with respect to the second compound can be envisaged to provide luminescent hybrid nanomaterial according to the present disclosure. So for example, a second compound, which is other than a heterole or a tetraphenylethylene, may be envisaged to provide a luminescent hybrid nanomaterial according to the present disclosure. Also, the process of the present disclosure for the preparation of luminescent hybrid nanomaterial according to the present disclosure is easy, efficient, and provides this new type of highly emissive materials in high yield, under mild conditions and in a limited number of steps.

The invention claimed is:
1. A luminescent hybrid nanomaterial comprising:
    at least one inorganic nanomaterial comprising an inorganic first compound;
    and
    at least one second compound comprising a first aggregation-induced emission moiety,
        wherein the at least one second compound is grafted on at least part of a surface of the inorganic first compound, and
        wherein the at least one second compound has one of the following structures:

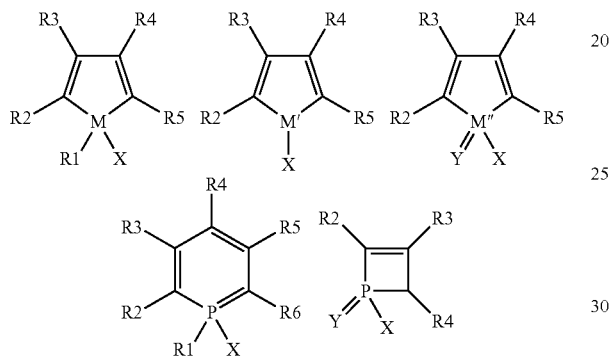

wherein:
    M is selected from the group consisting of Si, Ge, Sn and Pb;
    M' is selected from the group consisting of P, As, Sb and Bi;
    M" is selected from the group consisting of Si, Ge, Sn, Pb, P, As, Sb and Bi;
    X is selected from the group comprising H, OH, SH, SeH and TeH, or X is selected from the group comprising OR', SR', SeR' and TeR',
        R' being a first linker, the first linker comprising a first anchoring group, the first linker being a linear, cyclic or branched, saturated or unsaturated, C1-C20 alkyl group,
        the first anchoring group being selected from the group comprising a hydroxyl, thiol, carboxylic acid, carboxylic acid ester, cyano, amino, amido, sulfinic acid, sulfonic acid, phosphonic acid, dithiophosphinic acid, phosphate, phosphoester, phosphothioester, phosphine oxide, phosphine sulfide, phosphine, and silanol group;
    Y is selected from the group consisting of O, S, Se and Te;
    R1 is selected from the group consisting of a cyano, amino, amido, carboxylic acid, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, C2-C20 carboxylic acid ester, C1-C20 alkylsulfinic acid, C1-C20 alkylsulfonic acid, C1-C20 alkylphosphonic acid, C1-C20 alkyldithiophosphinic acid, C1-C20 alkylphosphate, C1-C20 alkylphosphoester, C1-C20 alkylphosphine oxide, and C1-C20 alkylphosphine group; or R1 is selected from the group consisting of H, OH, SH, SeH and TeH, or R1 is selected from the group consisting of OR", SR", SeR" and TeR", R" being a second linker comprising a second anchoring group,
        the second linker being a linear, cyclic or branched, saturated or unsaturated, C1-C20 alkyl group,
        the second anchoring group being selected from the group consisting of a hydroxyl, thiol, carboxylic acid, carboxylic acid ester, cyano, amino, amido, sulfinic acid, sulfonic acid, phosphonic acid, dithiophosphinic acid, phosphate, phosphoester, phosphothioester, phosphine oxide, phosphine sulfide, phosphine, and silanol group;
    each R2 to R6 is independently selected from the group consisting of a hydrogen, hydroxy, nitro, nitroxy, nitroso, halide, cyano, isothiocyanato, amino, amido, imino, azido, cyanato, isocyanato, polyethylene glycol, polypropylene glycol, C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione, C2-C20 alkylcarbonate, carboxylic acid, C2-C20 carboxylic acid ester, sulfinic acid, C1-C20 alkylsulfinyl, sulfonic acid and C1-C20 alkylsulfonyl group.

2. The luminescent hybrid nanomaterial according to claim 1, wherein the first aggregation-induced emission moiety comprises:
    a first cyclic conjugated substituent; and
    a second substituent conjugated with the first cyclic conjugated substituent.

3. The luminescent hybrid nanomaterial according to claim 2, wherein the first cyclic conjugated substituent is selected from the group comprising an heterole, and a phenyl group.

4. The luminescent hybrid nanomaterial according to claim 2, further comprising a restricted intramolecular rotation of the second substituent with respect to the first cyclic conjugated substituent.

5. The luminescent hybrid nanomaterial according to claim 2, wherein the second substituent is cyclic.

6. The luminescent hybrid nanomaterial according to claim 2, wherein the first aggregation-induced emission moiety further comprises a first linking moiety selected from the group consisting of an ether, a linear C1-C2 alkyl, C2 alkenyl and C2 alkynyl group, the first linking moiety connecting the first cyclic conjugated substituent to the second substituent.

7. The hybrid nanomaterial according to claim 1, wherein R2 and R3, or R3 and R4, or R4 and R5, or R5 and R6 form together a ring system.

8. The hybrid nanomaterial according to claim 1, wherein the at least one second compound has one of the following structures:

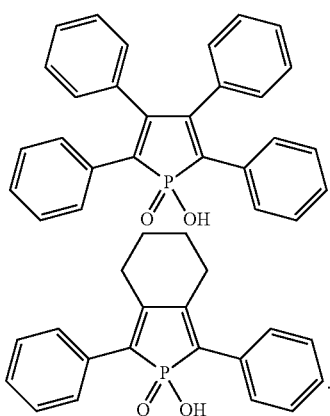

9. The hybrid nanomaterial according to claim 1, wherein the at least one second compound further comprises a second aggregation-induced emission moiety and/or a third substituent, which is an additional cyclic conjugated moiety, and/or at least one additional substituent selected from the group comprising a solubilizing moiety, a self assembly group, a chiral group, an oligomer and a polymer.

10. A process of manufacture of a luminescent hybrid nanomaterial according to claim 1, the process comprising:
providing the at least one inorganic nanomaterial comprising the inorganic first compound;
providing the at least one second compound; and
contacting the at least one second compound to at least part of the surface of the inorganic first compound, under conditions appropriate to graft or physisorb the at least one second compound on the surface of the inorganic first compound thereby forming the luminescent hybrid nanomaterial.

11. A product comprising the luminescent hybrid nanomaterial according to claim 1, wherein the product is selected from the group consisting of a thin film, a luminescent solar concentrator, a light-emitting hybrid diode or a light-emitting hybrid field-effect transistor.

* * * * *